US010340043B2

(12) United States Patent
Luo

(10) Patent No.: US 10,340,043 B2
(45) Date of Patent: Jul. 2, 2019

(54) SYSTEM AND METHOD FOR LOGISTICAL MANAGEMENT, SUPPORT AND SUPPLY OF OBJECTS

(71) Applicant: Butterfly Healthcare Pty. Ltd., Sydney, New South Wales (AU)

(72) Inventor: Qianping Luo, Sydney (AU)

(73) Assignee: Butterfly Healthcare Pty. Ltd., Sydney (AU)

( * ) Notice: Subject to any disclaimer, the term of this patent is extended or adjusted under 35 U.S.C. 154(b) by 242 days.

(21) Appl. No.: 15/128,680

(22) PCT Filed: Mar. 24, 2015

(86) PCT No.: PCT/IB2015/052161
§ 371 (c)(1),
(2) Date: Sep. 23, 2016

(87) PCT Pub. No.: WO2015/145358
PCT Pub. Date: Oct. 1, 2015

(65) Prior Publication Data
US 2017/0109483 A1    Apr. 20, 2017

(30) Foreign Application Priority Data
Mar. 24, 2014  (AU) .................................. 2014901050

(51) Int. Cl.
*G16H 40/20* (2018.01)
*G06Q 10/06* (2012.01)
(Continued)

(52) U.S. Cl.
CPC ............. *G16H 40/20* (2018.01); *G06F 19/00* (2013.01); *G06Q 10/06* (2013.01); *G06Q 10/087* (2013.01); *G06Q 10/1097* (2013.01)

(58) Field of Classification Search
CPC ........ G16H 40/20; G06F 19/00; G06Q 10/06; G06Q 10/087; G06Q 10/1097
See application file for complete search history.

(56) References Cited

U.S. PATENT DOCUMENTS 5,732,401 A * 3/1998 Conway ................ G06F 19/328
700/90
5,991,728 A * 11/1999 DeBusk ................ G06F 19/324
705/2

(Continued)

OTHER PUBLICATIONS

International Preliminary Report on Patentability issued in connection to International Application No. PCT/IB2015/052161 filed Mar. 24, 2015 "International Preliminary Report on Patentability" submitted on Jan. 21, 2016.

*Primary Examiner* — Nathan A Mitchell
(74) *Attorney, Agent, or Firm* — McKee, Voorhees & Sease, PLC

(57) ABSTRACT

A system and method for providing logistical management support of objects for consumption at one or more localities within a facility that sources the objects from a store. The system includes a server that allows subscribers to access relevant parts of datastore providing data on objects in the store. Devices are used by different subscribers to setup templates defining use of the objects in variety of situations in a dynamically scheduled manner. Applications operate on the devices for a particular subscriber to perform a task associated with using objects in accordance with different templates. Each application progresses the subscriber through functions involving the creation or performance of a procedure using the objects in accordance with a template. Some of the applications track the use of objects in real time and update the server and datastore with status information. The server communicates with an inventory management system to supplement the data with information concerning (Continued)

the availability and whereabouts of all objects specified in the templates. The server communicates with a booking system to determine when a procedure defined by a particular template will occur.

6 Claims, 29 Drawing Sheets

(51) Int. Cl.
  *G06Q 10/08* (2012.01)
  *G06Q 10/10* (2012.01)
  *G06F 19/00* (2018.01)

(56) References Cited

U.S. PATENT DOCUMENTS

| | | | | |
|---|---|---|---|---|
| 6,581,204 | B2* | 6/2003 | DeBusk | G06F 17/30 717/120 |
| 7,065,501 | B1 | 6/2006 | Brown et al. | |
| 2001/0016821 | A1* | 8/2001 | DeBusk | G06F 17/30 705/2 |
| 2002/0082866 | A1* | 6/2002 | Ladouceur | G06Q 40/04 705/2 |
| 2005/0149356 | A1* | 7/2005 | Cyr | G06Q 10/087 705/2 |
| 2005/0149379 | A1* | 7/2005 | Cyr | G06Q 10/10 705/2 |
| 2007/0112649 | A1* | 5/2007 | Schlabach | G06Q 10/087 705/28 |
| 2008/0270176 | A1* | 10/2008 | Andersen | G06Q 50/22 705/2 |
| 2009/0037244 | A1* | 2/2009 | Pemberton | G06Q 10/087 705/28 |
| 2009/0228302 | A1* | 9/2009 | Rothschild | G06Q 30/02 705/3 |
| 2011/0173028 | A1* | 7/2011 | Bond | G06Q 10/08 705/3 |
| 2012/0041770 | A1* | 2/2012 | Philippe | G06Q 10/087 705/2 |
| 2012/0239410 | A1* | 9/2012 | Bergstrom | G06F 19/325 705/2 |
| 2013/0066647 | A1* | 3/2013 | Andrie | G06Q 10/06311 705/2 |
| 2014/0249515 | A1* | 9/2014 | Martin | A61B 17/00 606/1 |
| 2015/0127366 | A1* | 5/2015 | ElLaissi | G16H 40/20 705/2 |
| 2015/0187035 | A1* | 7/2015 | Hogan | G06Q 50/22 705/2 |

* cited by examiner

SYSTEM AND METHOD FOR LOGISTICAL MANAGEMENT, SUPPORT AND SUPPLY OF OBJECTS

CROSS-REFERENCE TO RELATED APPLICATIONS

This application is the National Stage of International Application No. PCT/IB2015/052161, filed Mar. 24, 2015, which claims priority to and benefit of Australian Patent Application No. 2014901050, filed on Mar. 24, 2014, all of which are herein incorporated by reference in their entirety for all purposes.

FIELD OF THE INVENTION

The present invention relates to the logistical management, support and supply of objects for consumption or use on a dynamic basis at one or more localities within a precinct or facility that sources the objects from a common store. Further, the invention has particular utility in an environment where the consumption or use of the objects is prescribed according to a multiplicity of different recipes or templates in a variety of different procedures or processes that are performed according to a dynamic schedule.

An example of such a precinct or facility may be a hospital, where:
the localities are surgical theatres within the hospital;
the objects are surgical supplies such as surgical instruments, tools, implants, prosthetic devices etc. that are consumed or used in a surgical procedure;
the recipes or templates are surgeons' preference cards; and
the procedures or processes are surgical procedures or process such as post-surgery wound care.

An example of another precinct or facility may be a hotel or restaurant precinct, where the localities are different kitchens supplying various restaurants within the hotel or precinct, the objects are ingredients for meals that are consumed within the restaurants, the recipe or template are the particular ingredients required for the meals that are provided by the chef, and the procedures or processes are the recipes followed for preparing the different dishes or meals.

The invention also finds utility in extending these logistical management, support and supply functions enterprise wide for a precinct or facility such as a hospital or hotel where different departments or sections of the facility have similar inventory supply issues and overlapping functions with those provided by the surgical theatres or restaurants.

The invention also has useful outcomes related to work and health safety issues of clinicians and patients of hospitals more broadly.

Throughout the specification, unless the context requires otherwise, the word "comprise" or variations such as "comprises" or "comprising", will be understood to imply the inclusion of a stated integer or group of integers but not the exclusion of any other integer or group of integers.

Also the following terms will be used to cover the particular class of items indicated:

'Facility' will be used to cover both 'precinct' and 'facility' and any other type of geographical area that may have one or more localities within it that can be supplied by a common store.

'Store' is intended to mean any type of warehouse, pantry, storeroom or the like where objects for consumption or use may be stored as stock on a short term basis prior to being consumed or used.

'Object' is intended to mean any type of consumable stock item or ingredient that needs to be supplied for use in a procedure or process. For example, in a surgical procedure, an object can be any one or all of a surgical instrument, surgical tool, medical device, implant, prosthetic device or the like. In a meal or dish, an object is any type of food ingredient that may be used in the preparation of the meal or dish.

'Template' will be used to cover both 'recipe' and 'template' and any other prescribed list of objects that are required to be available for use in a particular procedure or process.

'Procedure' will be used to cover both 'process' and 'procedure' and any other methodology or descriptor for identifying a specialised set of steps that are performed to provide a particular outcome or deliverable. For example, in the hospital application, a procedure may be a particular type of surgical procedure, such as a knee replacement, organ replacement or removal, bone fixing etc. In a hotel environment, a procedure may be a particular type of dish that is available on the menu of a restaurant, for example Steak Diane, Beetroot ravioli, Beef pho, Crepe Suzette etc.

'Subscriber' is intended to mean any type of user of the system.

BACKGROUND ART

The following discussion of the background art is intended to facilitate an understanding of the present invention only. It should be appreciated that the discussion is not an acknowledgement or admission that any of the material referred to was part of the common general knowledge as at the priority date of the application.

In the healthcare industry, there are about 3 million surgeries performed in Australia each year.

Information relating to hospital operation, medical records and surgery performance is generally recorded manually in folders and paper documents for the purposes of record keeping, clinician co-ordination and procedure set-up and real time operation.

Surgeon's preference cards in the theatre are typically poorly maintained and not updated in a regular or consistent manner, due to lack of transparency and accessibility to relevant information.

Traditional surgical theatres generate considerable waste during theatre set up, and also as a consequence of performing actual surgery. A lack of practical inventory tools often results and so as a safeguard measure, a higher inventory holding rate is maintained than is actually needed. However, maintaining manual stock takes a considerable amount of theatre staff hours to support.

Hospital rebated items also tend to be forgotten and are often not added in to patient's records during surgery, resulting in financial losses for hospitals that can be avoided, but are justified out of the concern for patient safety.

With the increasing digitalisation of hospital processes, hospitals are sitting on extremely large amounts of data such as: financial, administrative, supply chain, patient and laboratory data, medical records, prescription, etc. The problem with this data is that it very often sits with different groups and departments within the organisation in isolation from each other. Consequently, this data is not being shared and is not being used effectively.

Furthermore, at present in Australia, there does not appear to be any system or method that is working efficiently in operating theatres that supplies stock information about objects in stored in the theatre storeroom to managers or administrators that allows for accurate purchasing decisions to be made.

Pre-operation safety checklists are also not being managed properly and clinicians tend to not be well informed prior to surgery. This is a big cause for concern with respect to patient safety and wastes a lot of staff hours to chase up all of the information when required, creating a lot of chaos in operating theatres.

Surgery bookings tend to be done between surgeon's rooms and hospitals via email or fax. Multiple data entries take a lot of time and there is gross dissatisfaction amongst clinicians and patients commencing from patient check-in.

Patient recovery time is generally never measured as a function of surgery performance and thus the "cost per surgery" is not being measured on a case-by-case basis.

Clinicians have been trained to focus on patient care, and are not specialised in object supply, paper based documents and the manual filling-in of information. Consequently, this wastes a lot of nurse hours and records are generally not retrievable unless a major accident happens.

Hospitals work on better disciplines with the training of nursing staff to type all cards in print format, color coding them for different specialties and tracking expensive items such as RFID scanner use, which is a rebatable item. Despite this, problems still remain due to:

Most if not all surgery records Australia wide still being paper-based, requiring manual data entry for any surgery records—inefficient paper systems cause a lot of stress for clinicians and wear out staff making for low job satisfaction. Surgeons' preference cards tend to never be updated on a regular basis, resulting in the loss of tracking information on the latest updated cards.

No real time data collection of usage information.

Experience and memory being used to base recordings of object usage data in the theatre for patients, resulting in human error which cannot be avoided and mistakes that are not easily traceable if minimal time is required.

No simple platform for capturing data in respect of usage information of objects and rebatable items.

Existing systems are complicated and only apply to warehousing, office administration and accounting—there is not any system or method that can be used for operating theatres, and supplying stock information in respect of the theatre storeroom.

Loose tracking of consignment stocks and loan kits. For example, an estimated AUD 1.26 million was consumed for clarifying prostheses rebated codes last year, and an estimated AUD 8.75 million was lost in revenue from unclaimed joint replacement prostheses. Loose tracking of critical medical devices causes high risks for patient safety and results in significant revenue loss for hospitals.

Whilst the aforementioned description has focused on the healthcare industry, many analogous problems are associated with the hospitality industry and the operation of a large hotel having several kitchens.

Even though the provision of a particular meal may not be essential to the point of being life threatening, nonetheless in terms of efficiency and variety in quality meal preparation and service delivery to the customer logistical management, support and supply issues and problems predominate. These similarly involve communication and ingredient supply problems, which if managed better can result in better efficiencies, customer satisfaction and staff tenure.

Disclosure of the Invention

It is an object of the present invention to provide for logistical management, support and supply of objects on a dynamic basis at one or more localities within a precinct of facility that sources the objects from a store that overcomes some or all of the problems outlined in the background art.

In one aspect of the invention, there is provided a software platform for delivering computer implemented, web accessible workflow management based on a SaaS model.

In another aspect of the present invention, there is provided a system for providing logistical management, support and supply of objects for consumption or use on a dynamic basis at one or more localities within a precinct or facility that sources the objects from a store, the system comprising:

an external processing system defining an environment that is operable to allow access by a plurality of subscribers to relevant parts of a data store providing master data on objects stored in the store;

a plurality of devices for use by one or more types of subscriber to setup templates defining the prescribed use of the objects in a variety of situations in a dynamically scheduled manner;

a plurality of applications for operating on the devices, each application being designed for a particular subscriber performing a prescribed task associated with the use of objects in accordance with different templates and to download relevant parts of the data store to store locally of the device;

each application adapted to progress the subscriber through a range of functions prescribed for the subscriber involving the creation or performance of a procedure or both the creation and performance of the procedure using some of the objects in accordance with a particular template, wherein some or all of the objects may be used or consumed in the procedure;

some or all of the applications adapted to track the use or consumption of the objects in the procedure in real time, and update the external processing system and data store with status information relating to same;

the external processing system communicating with an inventory management system to supplement the master data with information concerning the availability and whereabouts of all objects that may be specified in a template and tracked in the store;

the external processing system communicating with a dynamic scheduling system to determine when a procedure defined by a particular template will occur; and the external processing system organising the fetching of objects for delivery to the particular locality at a prescribed time for use or consuming in a scheduled procedure pursuant to the invoking of an application and progression of a subscriber through the specified range of functions therefor.

Preferably, one of the applications is a building application for one type of subscriber to create templates for use and populating by other subscribers.

Preferably, another of the applications is a setup application for another type of subscriber to select one or more templates associated with a group of templates related to a particular type of procedure or person, and populating the template with appropriate objects to be used in a procedure defined by the template.

Preferably, a further of the applications is procedural application associated with a group of templates defining a finished list of objects for use or consumption in a procedure; and updating the status of the objects in real time after they are used or consumed; and updating the data store in relation to such status.

Preferably the system is for a hospital, where the procedures are surgical procedures, the templates are surgeon's preference cards, and the objects are medical supplies.

In accordance with another aspect of the present invention, there is provided a method for providing logistical management, support and supply of objects for consumption or use on a dynamic basis at one or more localities within a precinct or facility that sources the objects from a store, the system comprising:

defining an environment that is operable to allow access by a plurality of subscribers to relevant parts of a data store providing master data on objects stored in the store;

one or more types of subscriber setting up templates defining the prescribed use of the objects in a variety of situations in a dynamically scheduled manner;

using different templates to prescribe task associated with the use of objects and downloading relevant parts of the data store to store locally of the device;

progressing the subscriber through a range of functions prescribed for the subscriber involving the creation or performance of a procedure or both the creation and performance of the procedure using some of the objects in accordance with a particular template, wherein some or all of the objects may be used or consumed in the procedure;

tracking the use or consumption of the objects in the procedure in real time, and updating the external processing system and data store with status information relating to same;

communicating with an inventory management system to supplement the master data with information concerning the availability and whereabouts of all objects that may be specified in a template and tracked in the store;

communicating with a dynamic scheduling system to determine when a procedure defined by a particular template will occur; and fetching objects for delivery to the particular locality at a prescribed time for use or consuming in a scheduled procedure pursuant to the invoking of an application and progression of a subscriber through the specified range of functions therefor.

Preferably, the system is for a hospital and the reports include patient care quality, diagnosis and treatment, clinical research, predictive analysis of diseases, inventory management, revenue capture, coding accuracy.

Preferably, the system is provides real time usage data to third party material suppliers and/or producers. In this manner, vendor inventory management based on the invention is able to replace traditional ordering processes, resulting in less waste and more accuracy, and minimising double handling.

BRIEF DESCRIPTION OF THE DRAWINGS

The invention is better understood in the light of the flowing description of the best mode for carrying out the invention. The description is made with reference to the following drawings that consist of schematic diagrams of various aspects of a system according to an embodiment of the present invention, and its operation and use; wherein:

FIGS. 26 to 29 are user interface shots applicable to the setup application.

BEST MODE(S) FOR CARRYING OUT THE INVENTION

The best mode for carrying out the invention is described in one specific embodiment directed towards a system and method for the logistical management, support and supply of objects used in a dynamically scheduled manner in the form of medical supplies for consumption or use on a dynamic basis at one or more localities being surgical theatres within a medical facility in the form of a hospital.

In this embodiment, the hospital has a local store in the form of a storeroom for storing medical supplies ready for surgical use planned within a prescribed time, for example 72 hours, before a surgical procedure or surgery in which the medical supplies are intended to be used, in relative close proximity to the surgical theatres where the surgery is to be performed.

Systemic Conceptual Overview

Figure 1:
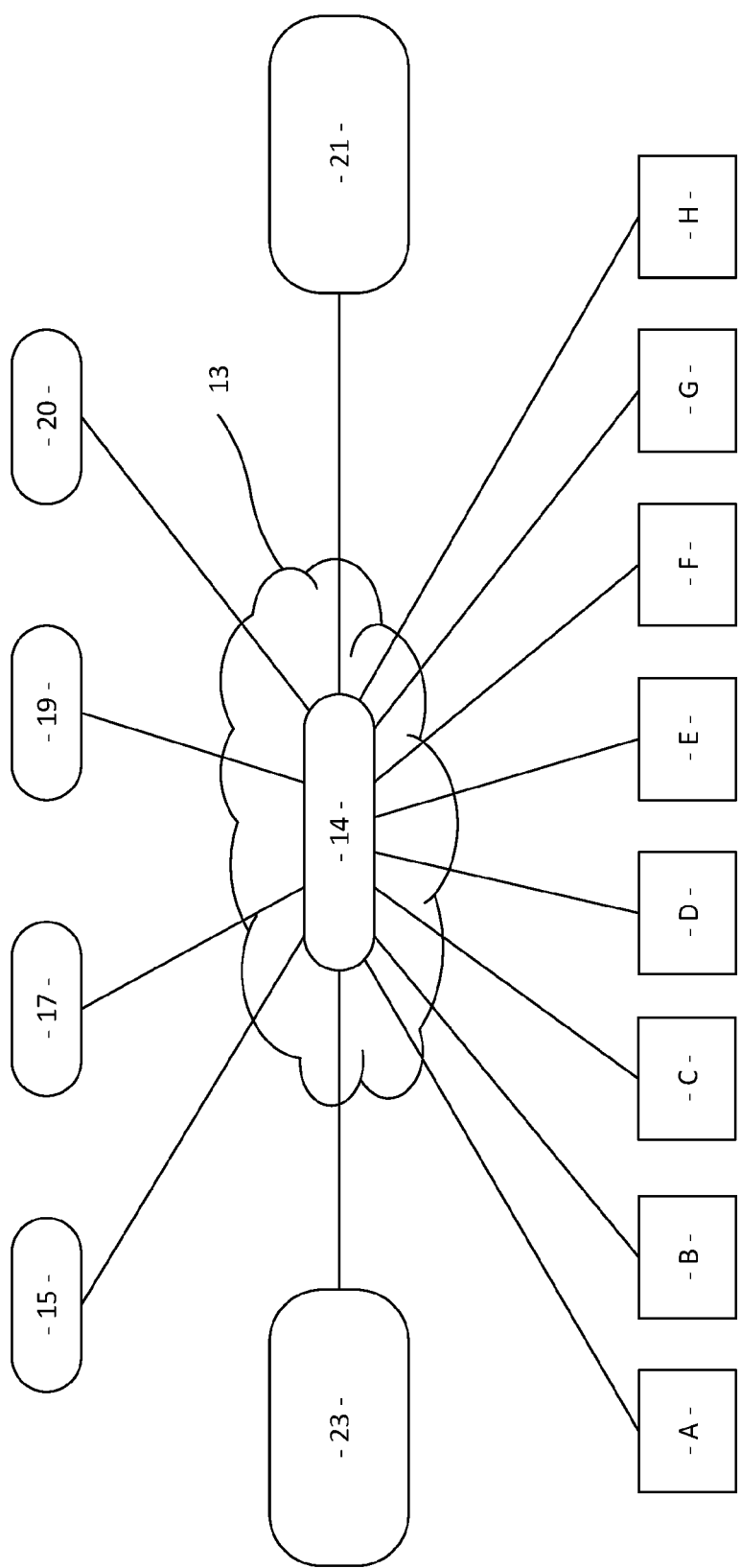
FIG. 1 is a schematic diagram of the system in conceptual overview.

As shown in FIG. 1 the system 11 in conceptual overview includes a cloud 13, being an interconnected electronic network for transmitting and receiving information, which connects users to various modules via an external processing system in the form of a hosted server 14.

The subscribers or users of the system 11 comprise hospital super users 15, clinicians 17, partners 19 and a system administrator 20, each performing a prescribed task and having a prescribed range of functions. The hospital super users 15 comprise hospital management and other administrators. Clinicians 17 comprise, for example, surgeons, anaesthetists and nurses. Partners 19 comprise third party providers of objects and supplementary services—such as medical suppliers (for example, of prosthetics), materials suppliers (for example, a glass company), or software suppliers (of, for example, an enterprise CRM system). The system administrator 20 comprises the computer system service provider responsible for supervising and administering the operation of the hosted server 14 and the technical aspects of the operation of the overall system 11.

Modules accessible to users comprise modules A to H, namely:
A. Window application for hospital management
B. Builder application for hospital management
C. Setup application involving surgeon's preference cards
D. Surgery application involving surgeon's preference cards
E. Setup application involving anaesthetist's preference cards
F. Surgery application involving anaesthetist's preference cards
G. Patient recovery/discharge application
H. Homecare application.

These modules A to H are sequenced according to a typical patient care pipeline that is end-to-end: from when the surgery is scheduled to recovery and convalescence.

Other modules 21 for partners 19, as indicated above, may be integrated for communication with the hosted server 14 in the cloud 13. These may be supplied by third parties, or provided as an extension of the modules A to H described above.

These other modules 21 can include accounting and financial systems, education/training modules etc., according to the needs of users.

The hosted server 14 in the cloud 13 also can receive information migrated for existing legacy hospital systems 23, which drives operation of the modules connected with the cloud, and interaction by users.

Although the system 11 is adapted to be integrated with modules E to H and other modules 21 and existing legacy hospital systems 23, for the purposes of describing the best mode for carrying out the subject invention, specific detail will be provided only in relation to the function and operation of modules A to D and in the context of users consisting of hospital super users 15 and clinicians 17.

Surgeon's Preference Cards

The foregoing description makes particular reference to accessing, editing and using surgeon's preference cards during building, setup for surgery and during actual surgery, data integration, booking and inventory management. Some aspects of the user interface of these preference cards are described with reference to user interface snapshots depicted in FIGS. 26 to 29.

A surgeon preference card system receives interaction from a number of users comprising a surgeon, a hospital manager 31, a hospital nurse 33, a scrub nurse 35, and a database and/or web administrator 20.

A surgeon edits his preference cards on the surgeon preference card system, either directly or via a nurse 33. The hospital manager 31 maintains user accounts, maintains categories and theatres, and builds preference cards using the surgeon preference card system. The nurse 33 sets up procedures on the surgeon preference card system. The web application developer 20 maintains and modifies the website using the surgeon preference card system. The database administrator maintains the database using the surgeon preference card system. The web administrator maintains hospitals, and maintains user accounts, and maintains products using the surgeon preference card system.

System Structure Diagram

Figure 2:
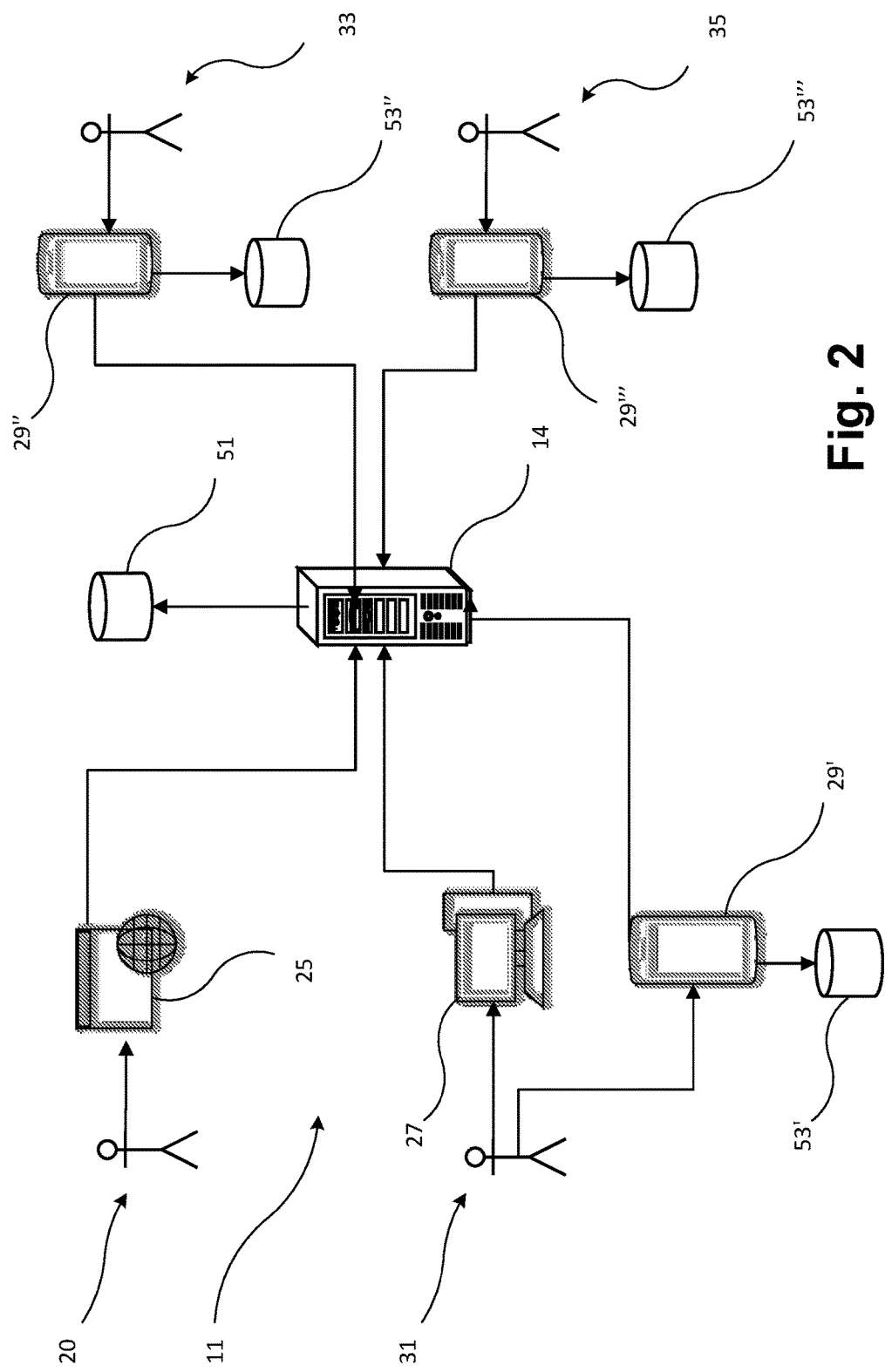
FIG. 2 is a schematic diagram of the system structure.

As shown in FIG. 2 the system structure centres on the hosted server 14, which provides a web service to different clients of the users of the system 11. These users comprise a system administrator 20 (the database and web administrator), a hospital manager 31, who is a super user 15, a nurse 33 and a scrub nurse 35, who are both clinicians.

The system administrator 20 has their own website 25 and accesses the server 14 from it. The system administrator 20 may administer a number of hospitals and controls all kinds of resources such as creating a new hospital for logistical management, support and supply of medical supplies. The data of one hospital is segregated from another with appropriate security, to form master data. The application modules are essentially the same and are used to maintain each hospital's inventory of products and supplies using the hosted server 14.

The hospital manager 31 has two modes to access the system 11. One via the window application A operated from client desktop 27 through which the hospital manager 31 can manage and maintain hospital user profiles, accounts, products categories, product types, theatre status and edit surgeons' or anaesthetists' preference cards using the hosted server 14.

The other mode of accessing the system 11 is via the builder application B operated from a mobile device, preferably a tablet 29'. Through the builder application B, the hospital manager 31 can build preference cards update surgeon pictures and product images.

The hospital nurse 33 accesses the system 11 via the setup application C, which is operated from a mobile device, preferably a tablet 29". Through the setup application C, the hospital nurse 33 can use preference cards such as pending cases and finished cases which are created by the builder application and setup procedure objects relative to a surgeon's or anaesthetist's preference using the hosted server 14.

The hospital scrub nurse 35 accesses the system 11 via the surgery application D, which is also operated from a mobile device, and preferably a tablet 29'''. The scrub nurse 35 accesses completed preferences cards via the server 14 for use in the prescribed surgery, which have previously been created by the setup application C to follow the specific surgery procedure and supply object items that are required for that surgery.

The hosted server 14 saves and fetches data from the master data for each hospital managed by the system 11 and each user via a database server 51, which in the present embodiment uses a Structured Query Language (SQL) for interrogating the database server.

Each of the mobile device tablets 29 use an embedded relational database management system (DBMS) 53 to hold data specific to each application, which in the present embodiment is SQLite. In the case of the builder application B, the tablet 29' saves and fetches local data to and from the DBMS 53'; in the case of the setup application C, the tablet 29" saves and fetches local data to and from the DBMS 53"; and in the case of the surgery application D, the tablet 29''' saves and fetches local data to and from the DBMS 53'''. Each DBMS 53 synchronizes this data via a web services of the server 14 with each registered application as appropriate.

Figure 3:
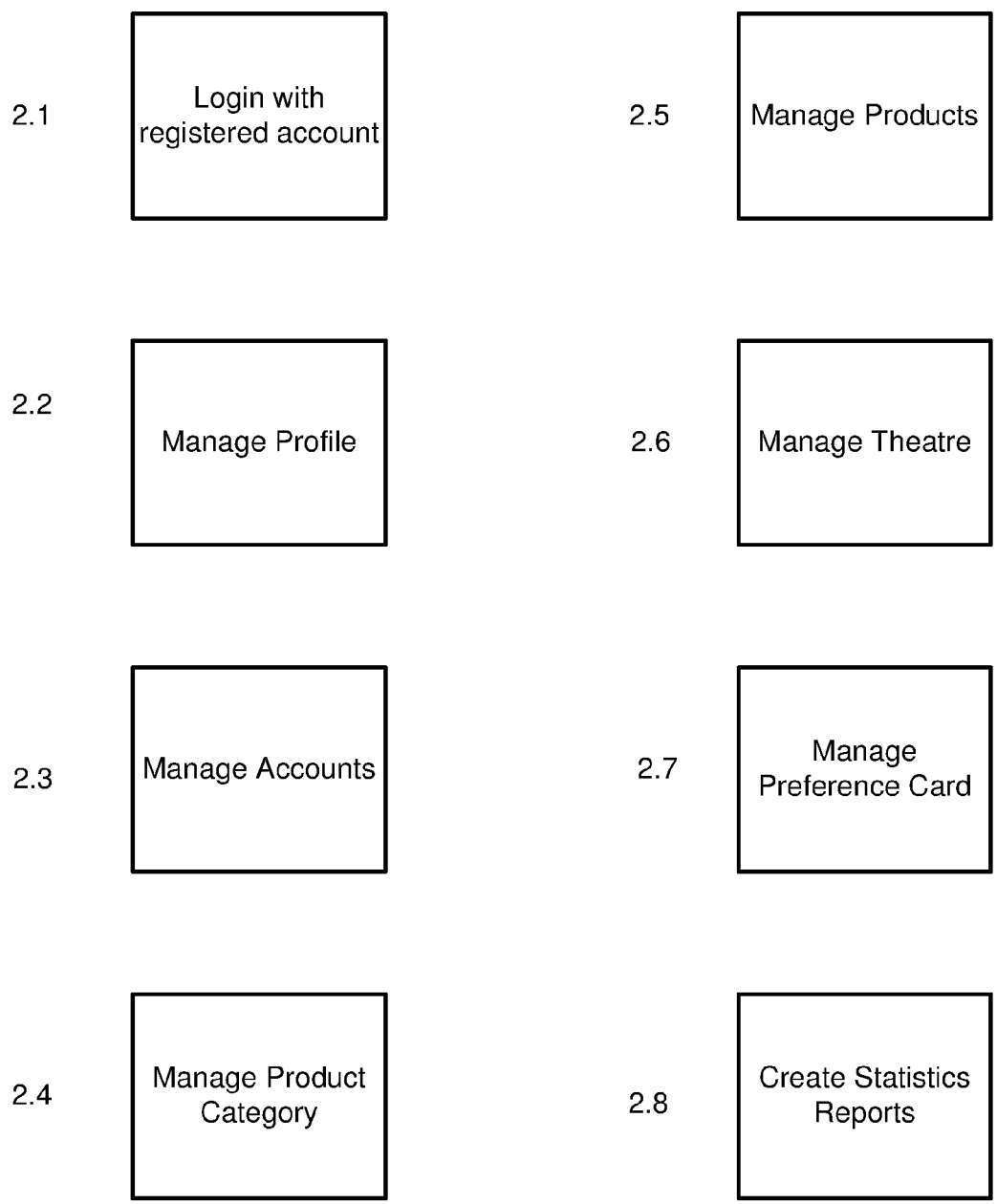
FIG. 3 is a block diagram showing the various menu options available for accessing the window application of the system for hospital managers.

As shown in FIG. 3, the window application A when invoked on a client desktop 27 provides various user selectable options to a hospital manager 31. Each of these options when selected in turn invokes a process to allow the hospital manager 31 to perform functions prescribed for the hospital manger super user 15. These options can be accessed with full permission after a login process 2.1 is successfully traversed to access the registered account of the hospital manager 31 on the system 11.

Options available to the hospital manager include: Manage Profile 2.2; Manage Accounts 2.3; Manage Product Category 2.4; Manage Products 2.5; Manage Theatre 2.6; Manage Preference Card 2.7; and Create Statistics Reports 2.8. The processes invoked by these options will be described in more detail later.

Figure 4:
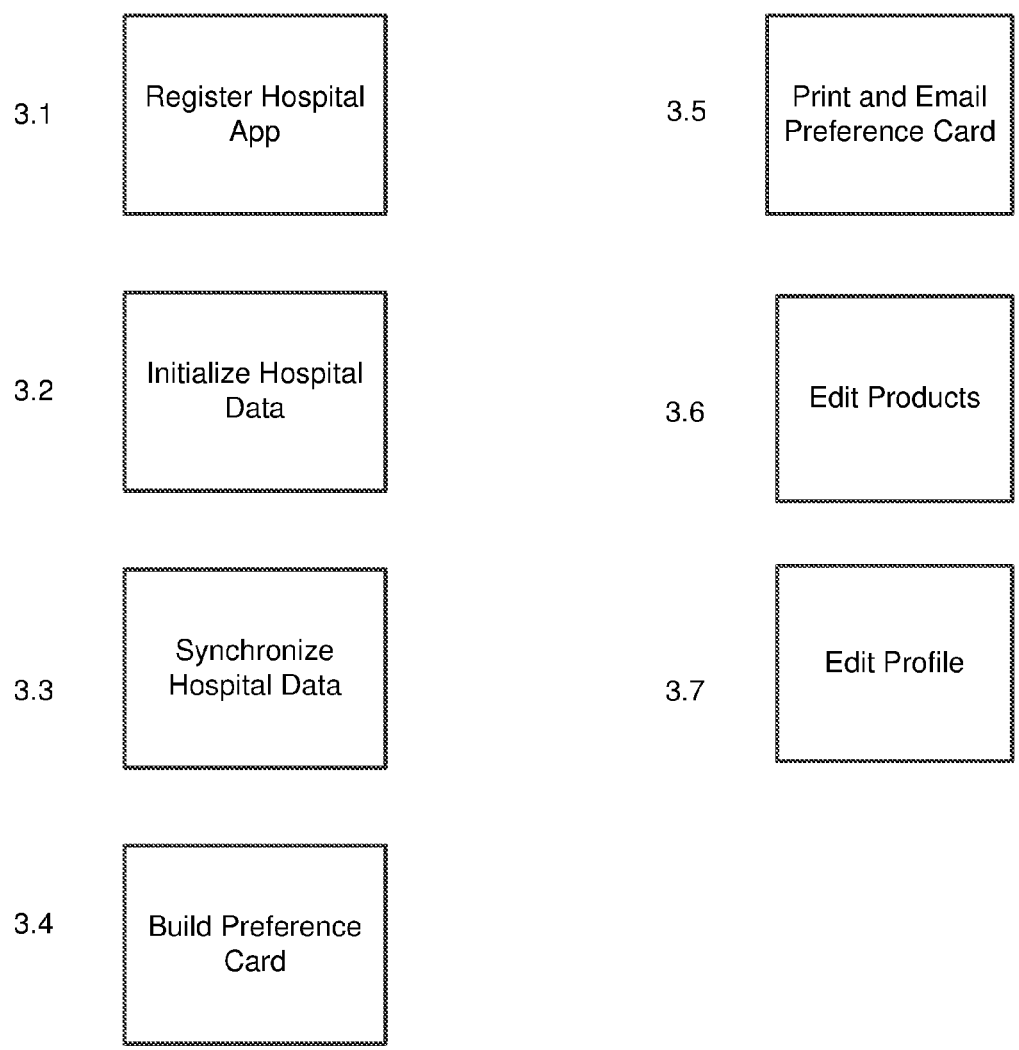
FIG. 4 is a block diagram showing the various menu options available for accessing the builder application of the system for hospital managers.

As shown in FIG. 4, the builder application B when invoked on a mobile device tablet 29' by a hospital manager 31, provides various user selectable options which can be accessed with full permission after a Register Hospital App option 3.1 is invoked and successfully traversed to register the access of the hospital manager on the system 11 via the App.

Options available via the builder application B to the hospital manager 31 include: Initialize Hospital Data 3.2; Synchronize Hospital Data 3.3; Build Preference Card 3.4; Print and Email Preference Card 3.5; Edit Products 3.6; and Edit Profile 3.7. The processes invoked by these options will be described in more detail later.

Figure 5:
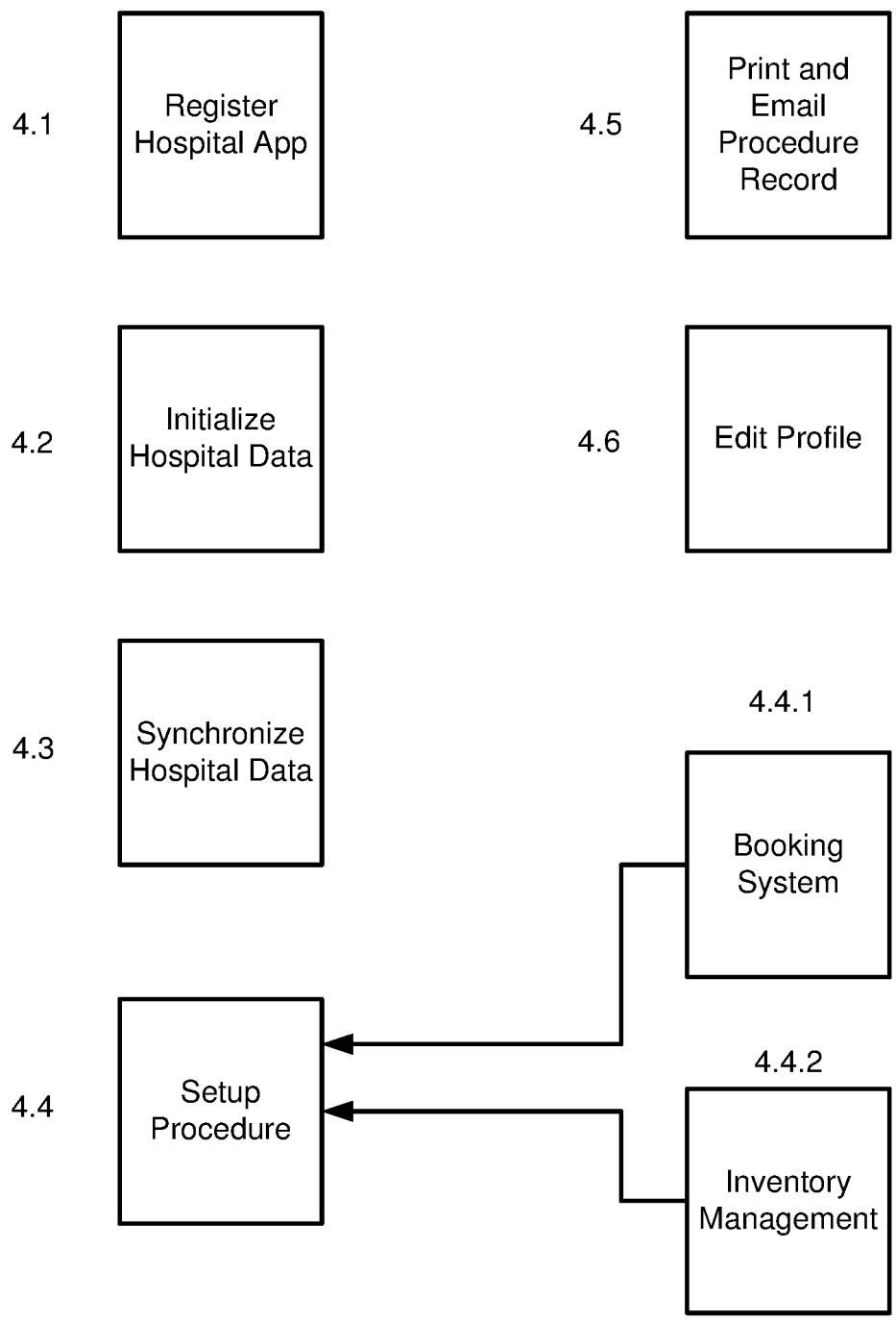
FIG. 5 is a block diagram showing the various menu options available for accessing the setup application of the system for hospital nurses.

As shown in FIG. 5, the setup application C when invoked on a mobile device tablet 29" by a hospital nurse 33 provides various user selectable options which can be accessed with full permission after a Register Hospital App option 4.1 is selected to invoke a Register Hospital App process for registering an instance of the use of the setup application permitting access of the nurse to the system 11.

Once the registration is completed, options available to the hospital nurse 33 by way of the setup application C include: Initialize Hospital Data 4.2; Synchronize Hospital Data 4.3; Setup Procedure 4.4, which branches to Booking System 4.4.1 and Inventory Management 4.4.2 options; Print and Email Preference Card 4.5; and Edit Profile 4.6. Certain of the processes invoked by these options will be described in more detail later.

Figure 6:
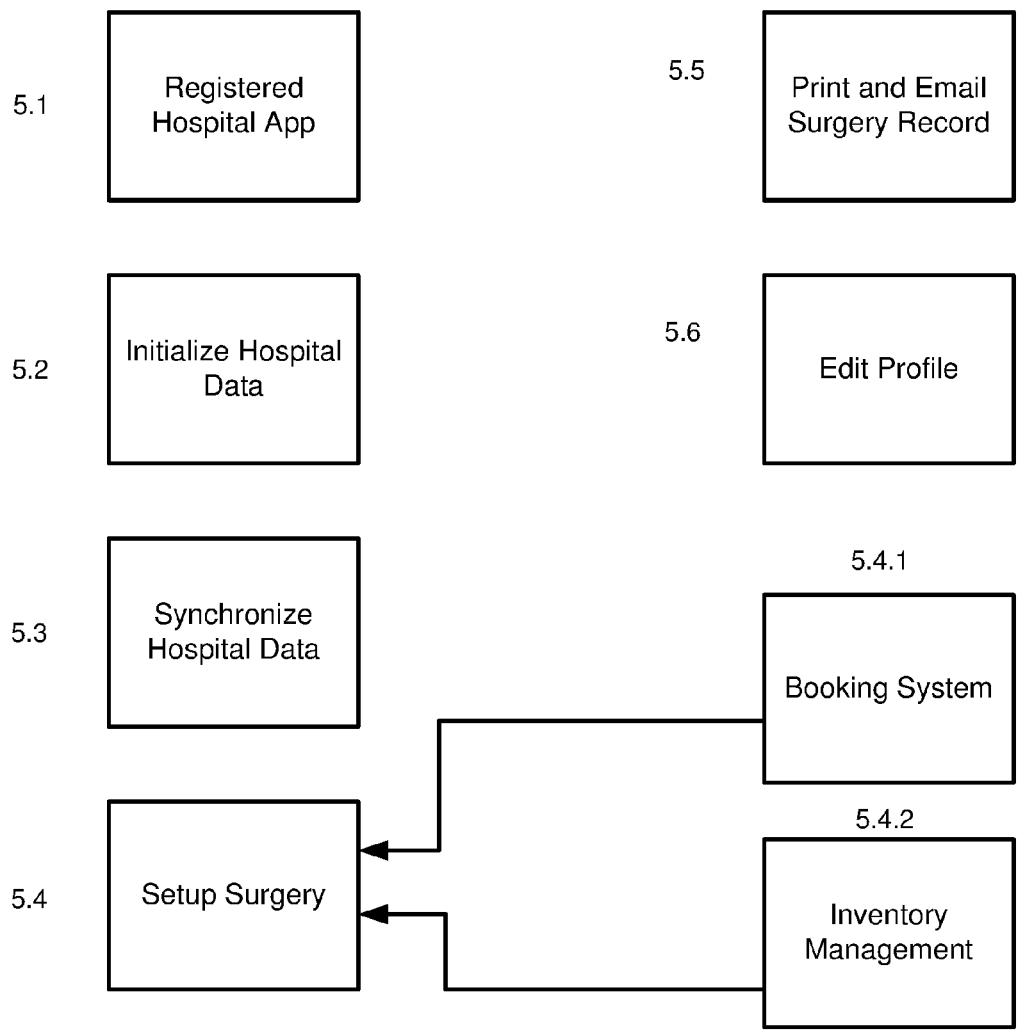
FIG. 6 is a block diagram showing the various menu options available for accessing the surgery application of the system for hospital scrub nurses.

As shown in FIG. 6, the surgery application D when invoked on a mobile device tablet 29''' by a hospital scrub nurse 35 provides various user selectable options which can be accessed with full permission after a Register Hospital App option 5.1 is selected to invoke a Register Hospital App process for registering an instance of the use of the surgery application permitting access of the scrub nurse to the system 11.

Once the registration is completed, options available to the scrub nurse 35 by way of the surgery application D include: Initialize Hospital Data 5.2; Synchronize Hospital Data 5.3; Setup Surgery 5.4 including Booking System 5.4.1 and Inventory Management 5.4.2 options; Print and Email Surgery Record 5.5; and Edit Profile 5.6. The processes invoked by these options and the preceding options will now be described.

Having regard to the window application A, selecting the Manage Profile 2.2 option invokes a Manage Profile process (not shown) that allows a hospital manager 31 to access and update their personal profile stored on the system 11, such as changing their password and/or updating their photo etc.

Figure 7:
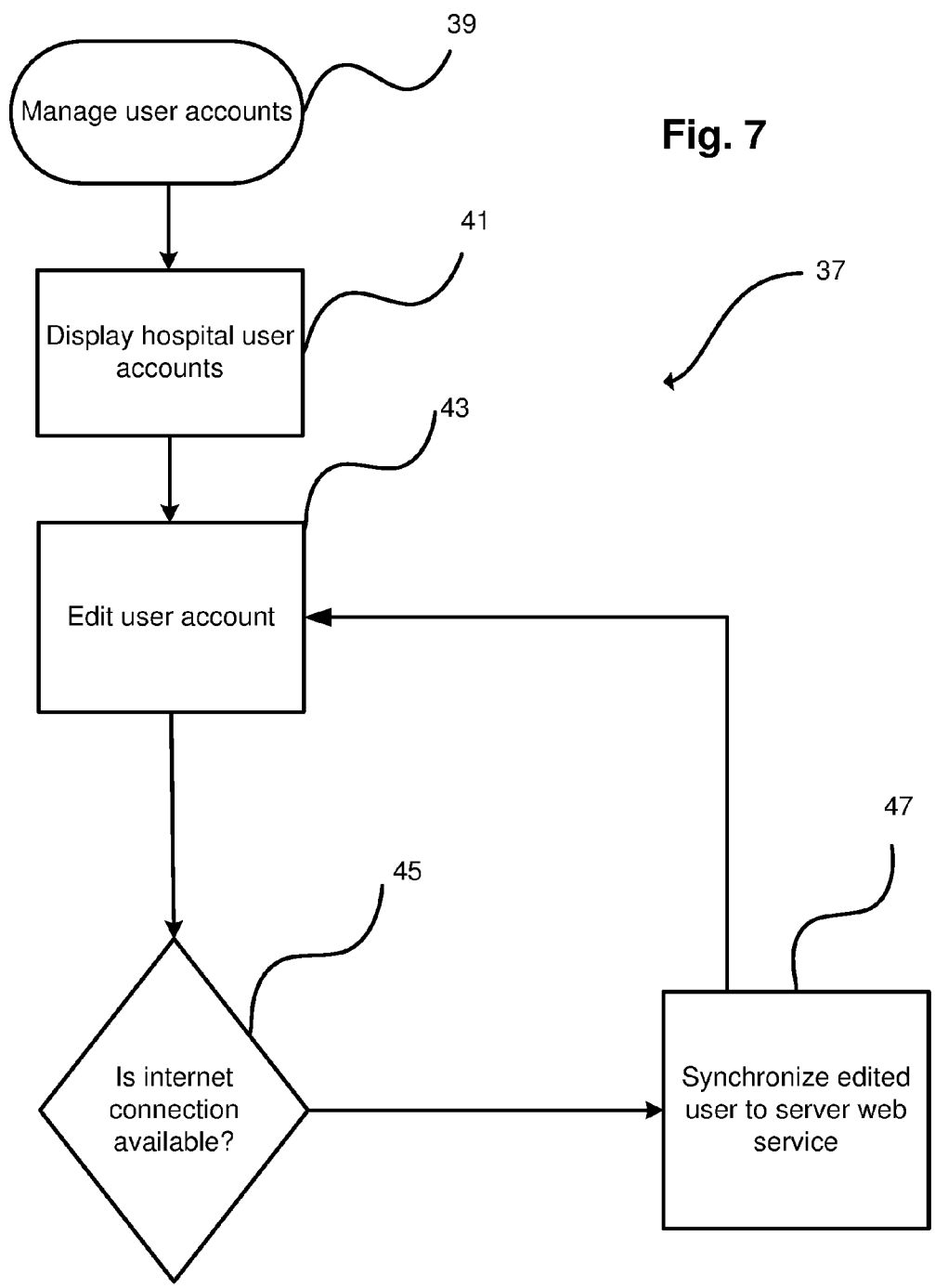
FIG. 7 is a flowchart showing the methodology of the Manage User Account process of the window application.

Selecting the Manage Accounts option 2.3 invokes a Manage User Account process 37, as shown in FIG. 7. The Manage User Account process 37 is used to add user accounts to the system 11 by importing user details received via data integration in a prescribed 'users.xls' file format or inputting the user details manually. The process 37 commences at step 39 and displays the various hospital user accounts at step 41. The process is programmed to allow the hospital manager 31 to edit a selected user account at step 43. Once the editing step is completed, the process advances to check whether an Internet connection is available at step 45, and if so, the process continues to synchronize the edits with the data stored on the database server 51 via the server web service at step 47. Subsequently, the process returns to the edit user account step 43 and permits further editing or exiting from the process.

Figure 8:
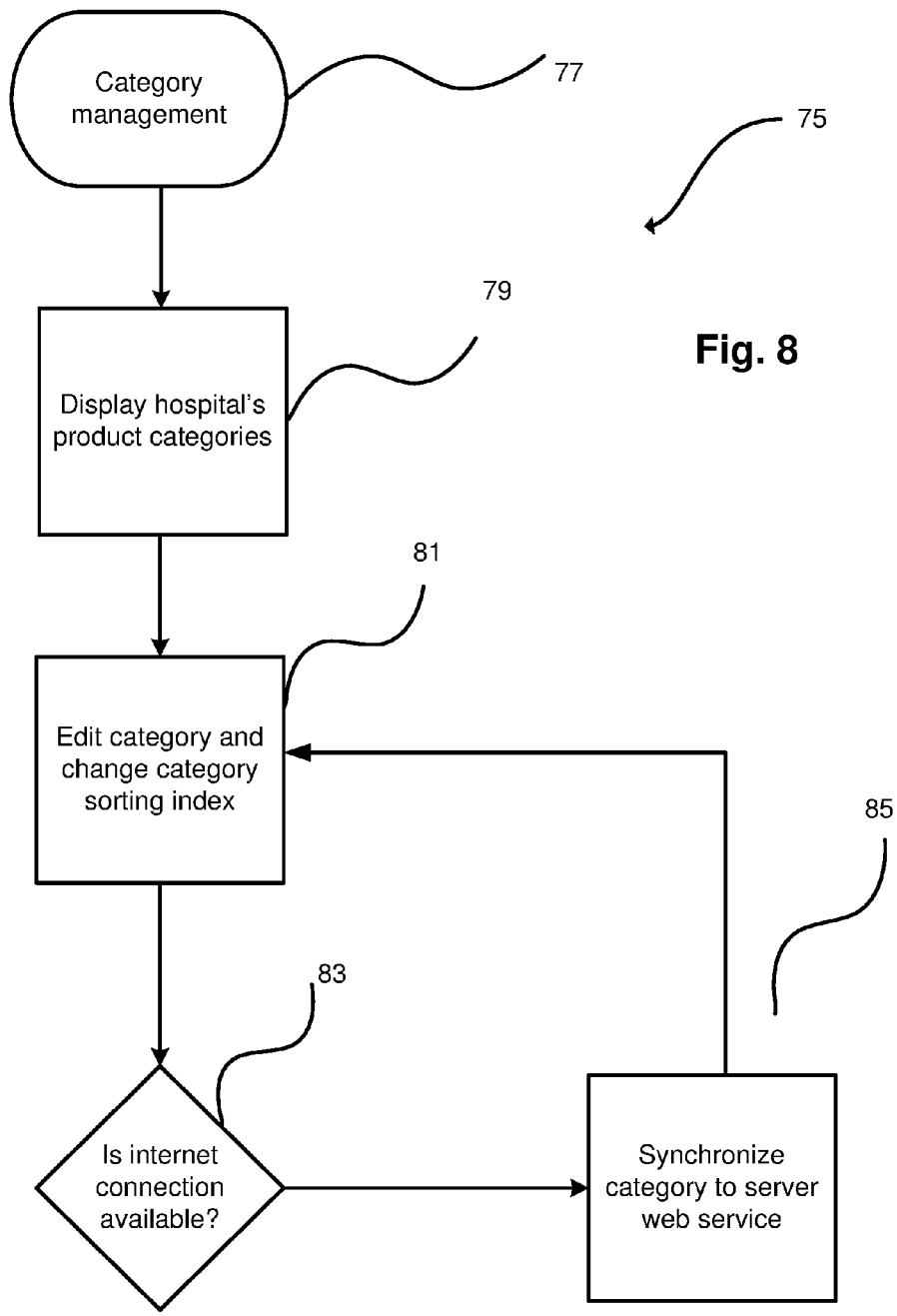
FIG. 8 is a flowchart showing the methodology of the Product Category Management process of the window application.

Selecting the Manage Product Category option 2.4 invokes a Product Category Management process 75 as shown in FIG. 8. The Product Category Management process 75 is used to change product categories to the system 11 by importing a 'category.xls' file from a data source that has previously been integrated with the system or inputting category detail information manually. The process can also be used to change the priority level of the product category within a product category hierarchy predetermined within the system for stock ordering purposes, depending upon the type of product and product category.

The Product Category Management process 75 commences at step 77 and displays the various hospital's product categories at step 79. The process is programmed to allow the hospital manager 31 to edit a selected category and change the category sorting index as necessary at step 81. Once the editing step is completed, the process advances to check whether an Internet connection is available at step 83, and if so, the process continues at step 85 to synchronize the category edits with the data stored on the database server 51 via the server web service. Subsequently, the process returns to the edit category step 81 and permits further editing or exiting from the process.

Figure 9:
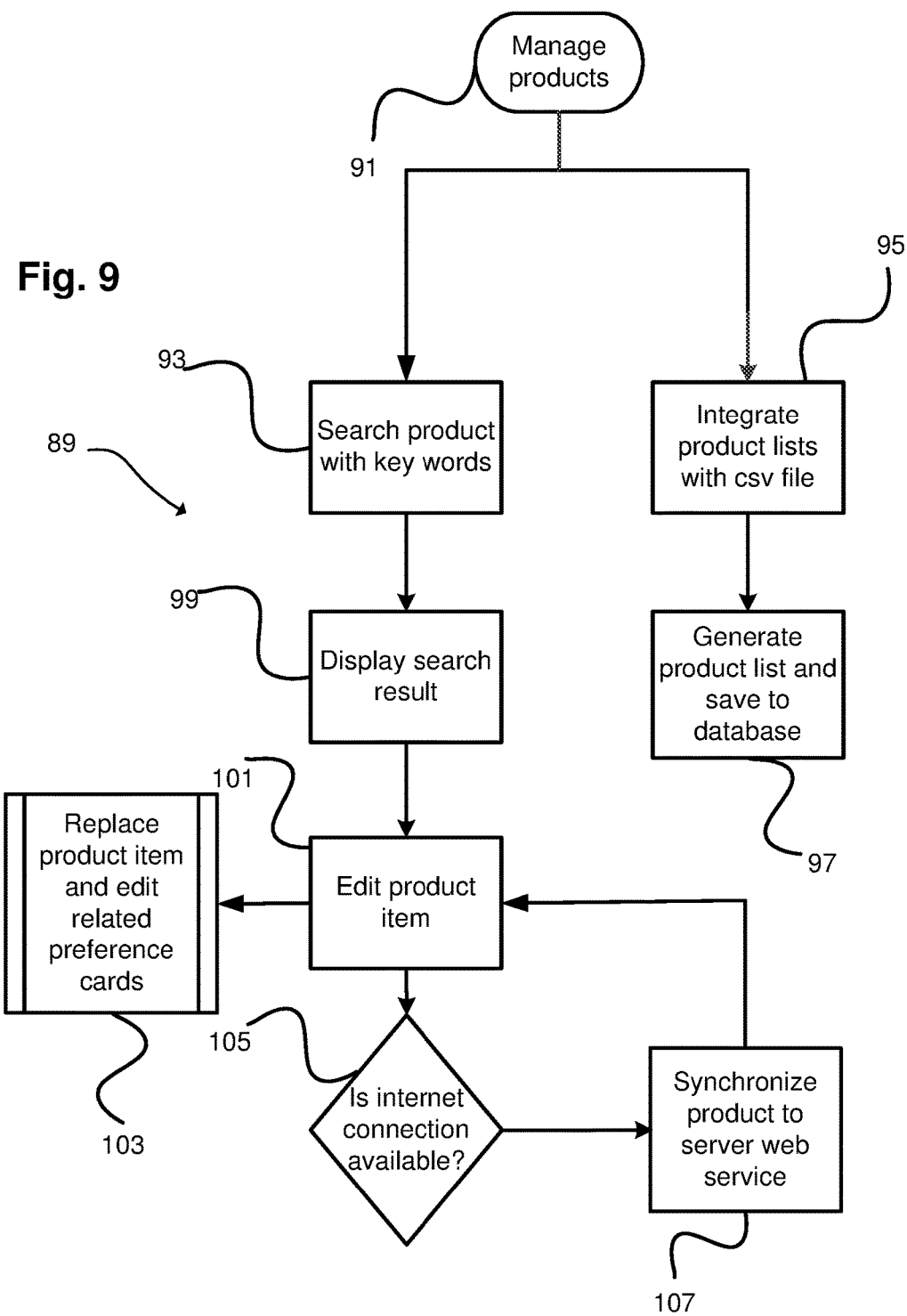
FIG. 9 is a flowchart showing the methodology of the Manage Products process of the window application.

Selecting the Manage Products option 2.5 invokes a Manage Products process 87 as shown in FIG. 9. The Manage Products process 89 allows new products to be added to the system by importing a 'product.xls' file or inputting product detail information manually. Product items can also be replaced through the process. The Manage Products process 89 commences at step 91 and provides the hospital manager 31 with two options, one to search for a desired product with key words at step 93 and the other to integrate the product list with csv file providing new product information at step 95. In the case of the latter, the process at step 97 proceeds to generate a new product list incorporating the new product information and saving this via the database server 51.

In the case of the hospital manager 31 invoking the search product option and entering one or more key words at step 93, the process proceeds with displaying the search result at step 99. The process is programmed to then allow the hospital manager 31 to edit the product item at step 101. If it is desired to replace the product item, then a replacement process is invoked at step 103, which includes the ability to edit related preference cards including the product item.

Once the editing step is completed, the process advances to check whether an Internet connection is available at step 105, and if so, the process continues at step 107 to synchronize the product edits with the data stored on the database server 51 via the server web service. Subsequently, the process returns to the edit product item step 101 and permits further editing or exiting from the process.

Figure 10:
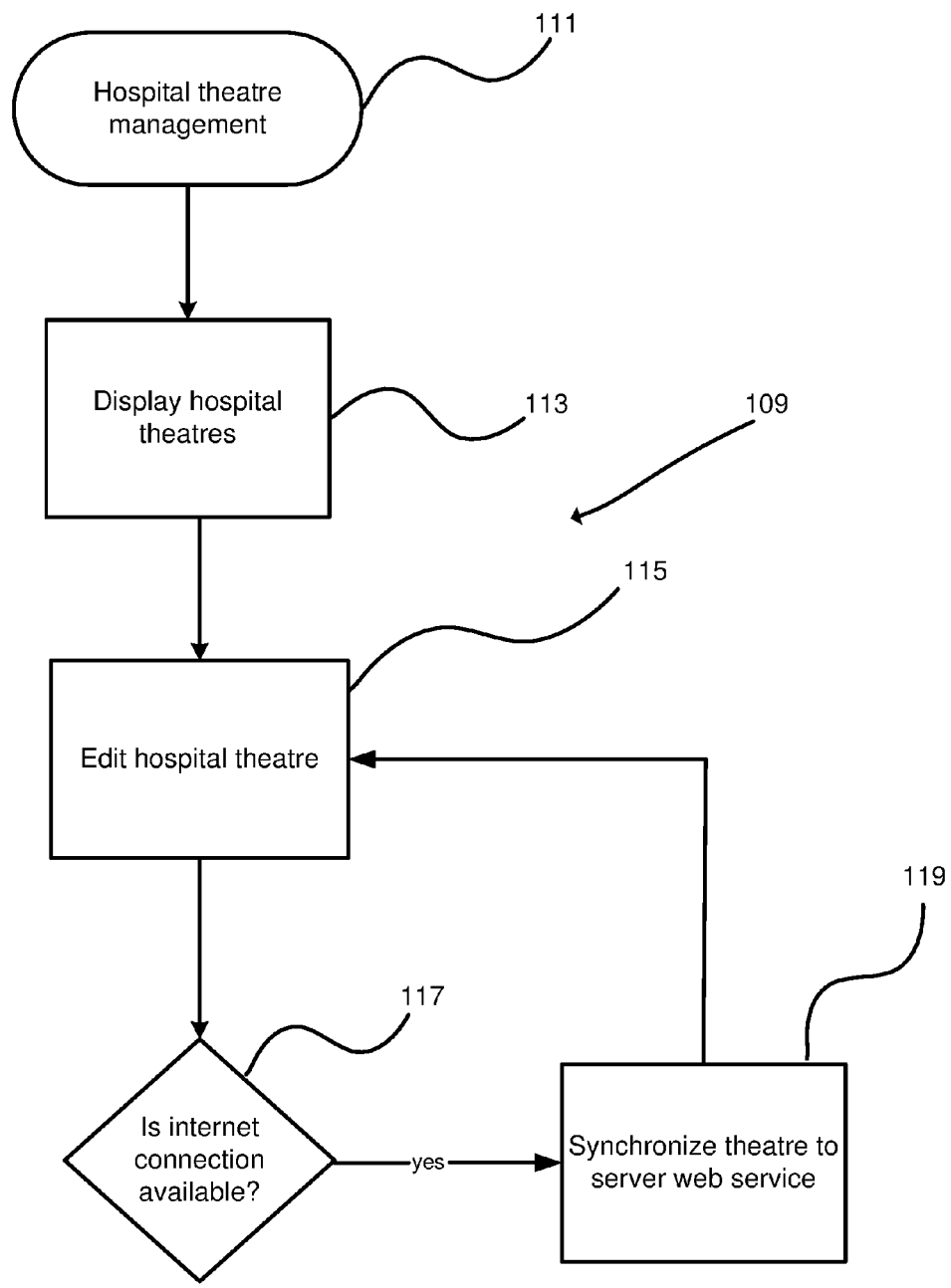
FIG. 10 is a flowchart showing the methodology of the Hospital Theatre Management process of the window application.

Selecting the Manage Theatre option 2.6 invokes a Hospital Theatre Management process 109 as shown in FIG. 10. The Hospital Theatre Management process 109 allows new surgical theatres to be added to the system by importing using a 'theatres.xls' file or inputting theatre detail information manually. The Hospital Theatre Management process 109 commences at step 111 and displays the various surgical theatres of the hospital at step 113. The process is programmed to allow the hospital manager 31 to edit the details of a listed hospital theatre at step 115. Once the editing step is completed, the process advances to check whether an Internet connection is available at step 117, and if so, the process continues at step 119 to synchronize the theatre edits with the data stored on the database server 51 via the server web service. Subsequently, the process returns to the edit theatre step 115 and permits further editing or exiting from the process.

Figure 11:
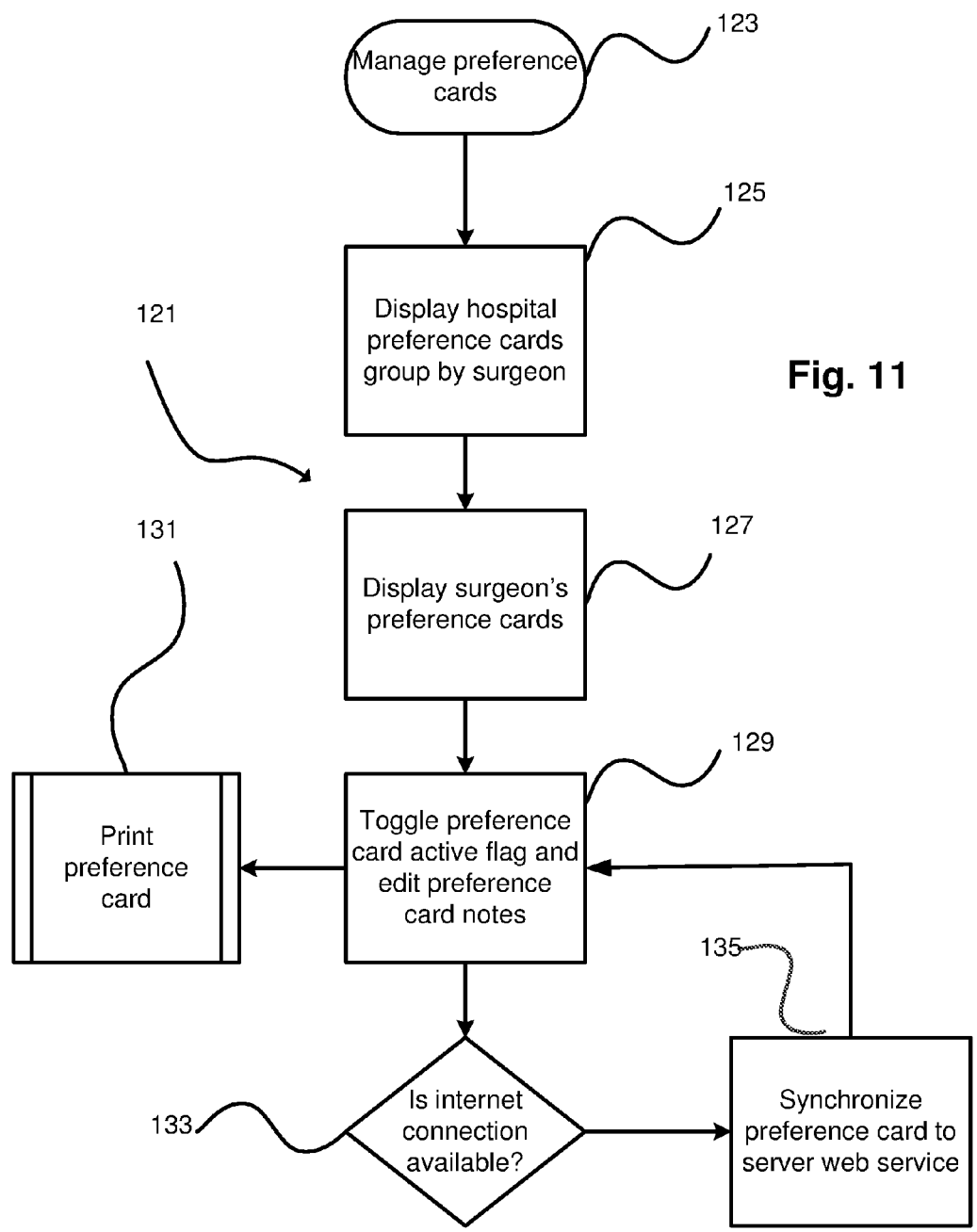
FIG. 11 is a flowchart showing the methodology of the Manage Preference Cards process of the window application.

Selecting the Manage Preference Card option 2.7 invokes a Manage Preference Cards process 121 as shown in FIG. 11. The Manage Preference Cards process 121 allows preference cards to be printed, renamed and status changed (active/deactive) to the system by the hospital manager 31. The Manage Preference Cards process 121 commences at step 123 and is programmed to display the various preference cards of the hospital as grouped by surgeon at step 125. It then allows a particular surgeon's preference card to be selected and displayed at step 127. The process then allows the hospital manager 31 to edit the status by toggling the active flag of a selected preference card and to edit the preference card notes at step 129. A preference card can then be printed at step 131 once the editing step is completed and/or the process advanced to check whether an Internet connection is available at step 133. If so, the process continues at step 135 to synchronize the preference card edits with the data stored on the database server 51 via the server web service. Subsequently, the process returns to the edit preference card step 129 and permits further editing of preference cards or exiting from the process.

Figure 12:
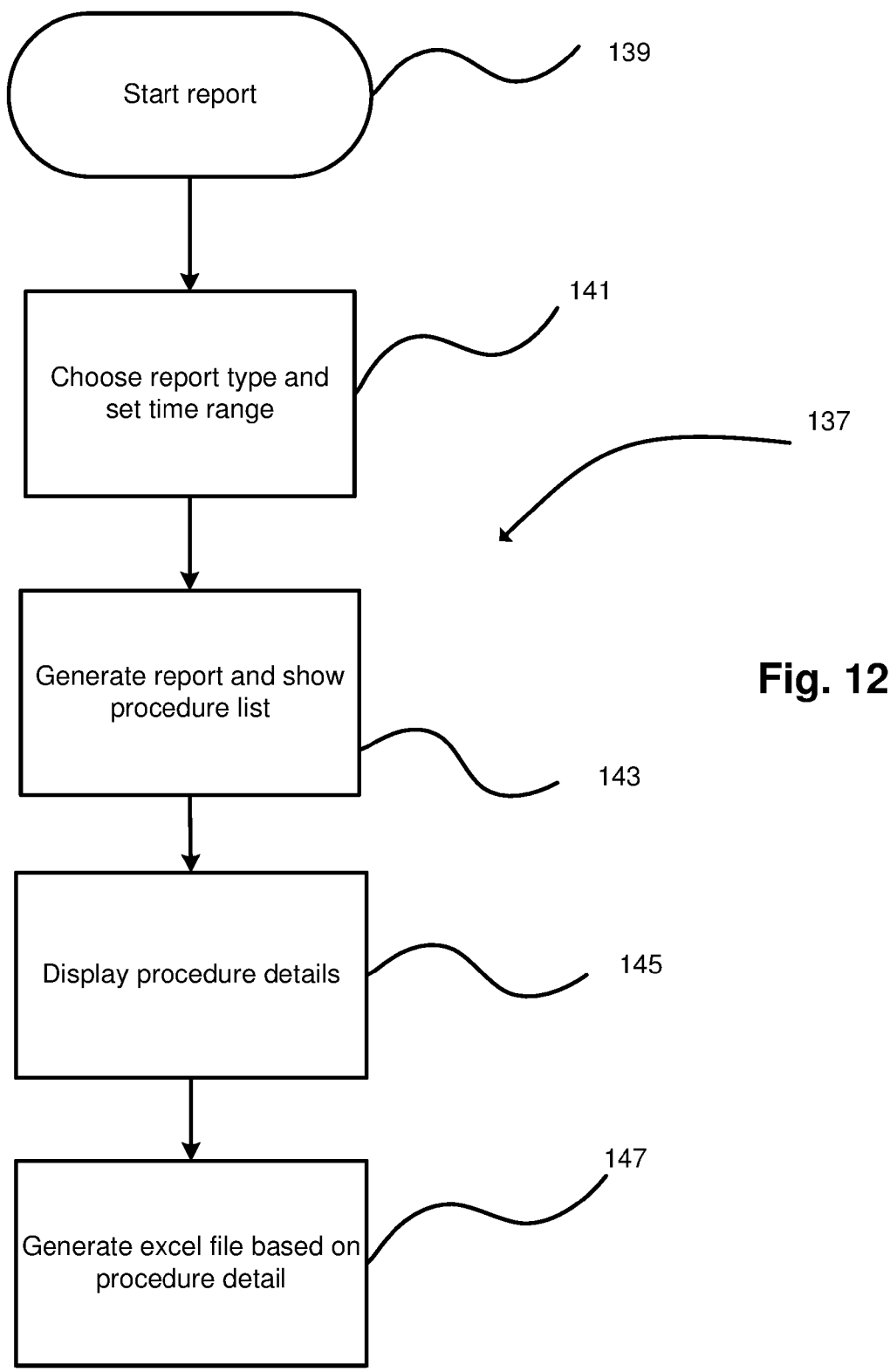
FIG. 12 is a flowchart showing the methodology of the Statistics Reports process of the window application.

Selecting the Manage Preference Card option 2.8 invokes a Create Statistics Reports process 137 as shown in FIG. 12. The Create Statistics Reports process 137 allows the hospital manager 31 to create a statistical report based on a date range and report the results in a format that can be of a particular format, e.g. Data Grid, Pie Chart, Column Chart etc. The Create Statistics Reports process 137 commences at step 139 and is programmed to allow the hospital manager to choose the report type and set the time range at step 141. It then generates the report at step 143 and shows the procedure list. The process proceeds to displaying the procedure details at step 145. The hospital manager 31 can then proceed to generating a spreadsheet file based on the procedure detail and store same at step 147.

Figure 13:
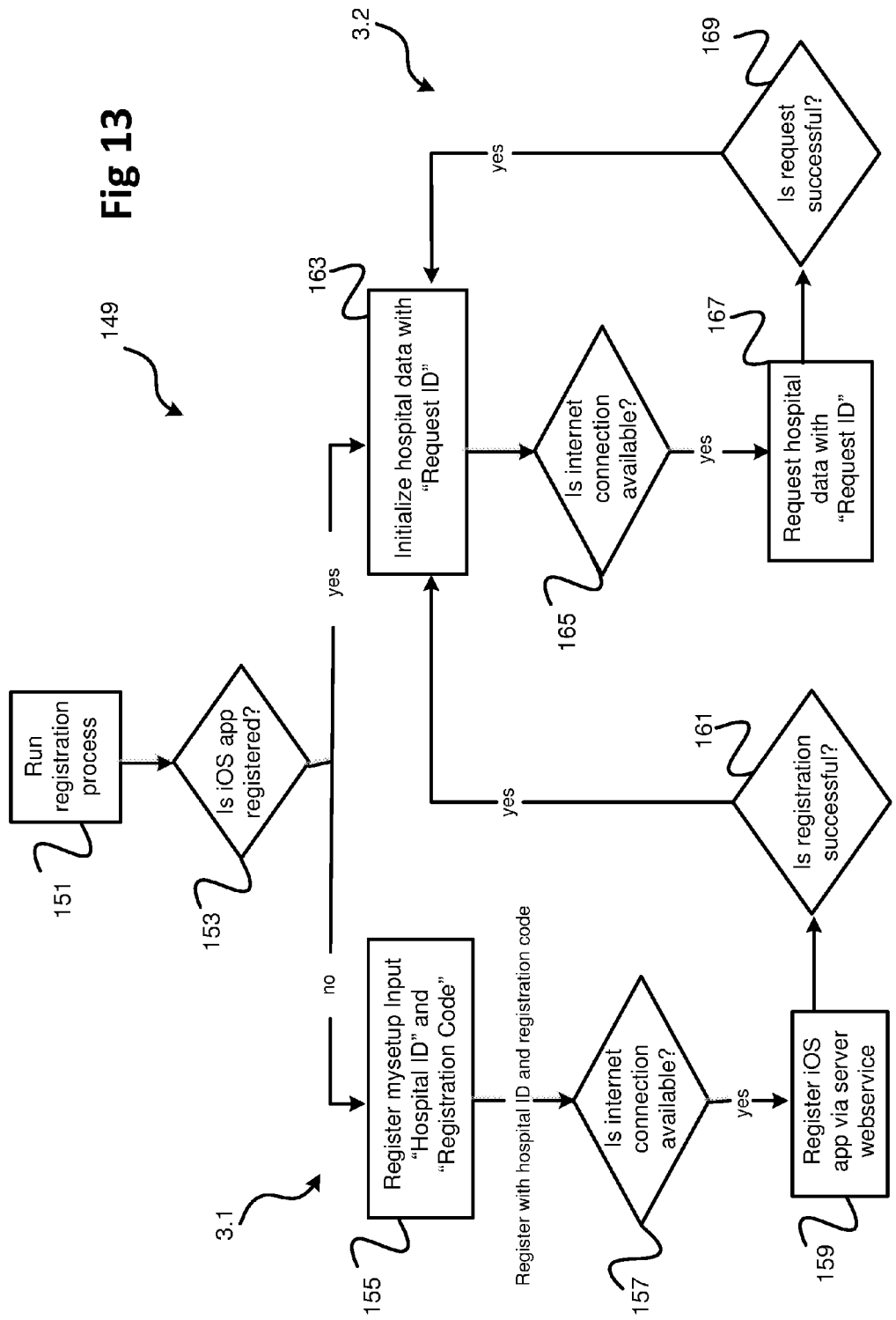
FIG. 13 is a flowchart showing the methodology of the Initialize Hospital Data process of the builder application.

Now having regard to the builder application B, the Register Hospital App option 3.1 and the Initialize Hospital Data option 3.2 are implemented as two discrete branches of a common Initialize Hospital Data process 149 as shown in FIG. 13. The Register Hospital App option 3.1 registers an instance of the App use for inputting data by the hospital manager 31 and the Initialize Hospital Data option 3.2, following registration, downloads relevant data from the database server 51 of the system 11 and stores it in the local DBMS 53' of the tablet 29' running the App.

The Initialize Hospital Data process 149 commences at step 151 to run the registration process initially. It firstly checks whether the instance of the App is registered on the system for use by the hospital manager at step 153 according to the permissions set for the hospital manager. If not, it then proceeds to register input from the App at step 155 as part of the Register Hospital App option 3.1, where the hospital manager is required to enter a Hospital ID code to identify the particular hospital with which the hospital manager is associated and a Registration Code comprising a serial number associated with the particular instance of use of the App known to the hospital manager, characterising the purpose to which the App is to be used. Once this information is entered the registration process advances to check whether an Internet connection is available at step 157, and if so, the process continues at step 159 to register the registration details of the App on the system 11 via the server web service. The process then checks with the system whether the registration has been successful at step 161 and if so, then proceeds to invoke the Initialize Hospital Data option 3.2.

In the event that the instance of App use is registered following step 153, or successfully completing the Register Hospital App option 3.1 following step 161, the Initialize Hospital Data process 149 proceeds to initialize the transfer of hospital data to the DBMS 53' of the device 29' at step 163 by recording the Request ID generated by the device for the particular App instance. The Initialize Hospital Data process 149 then proceeds to check whether an Internet connection is available at step 165. If so, the process continues at step 167 to request the appropriate hospital data associated with the particular Request ID to be downloaded to the tablet device 29'. The success of the download request is then checked at step 169 and if so, the process returns to the start of the initialization step 163 to permit exiting from the process.

Figure 14:
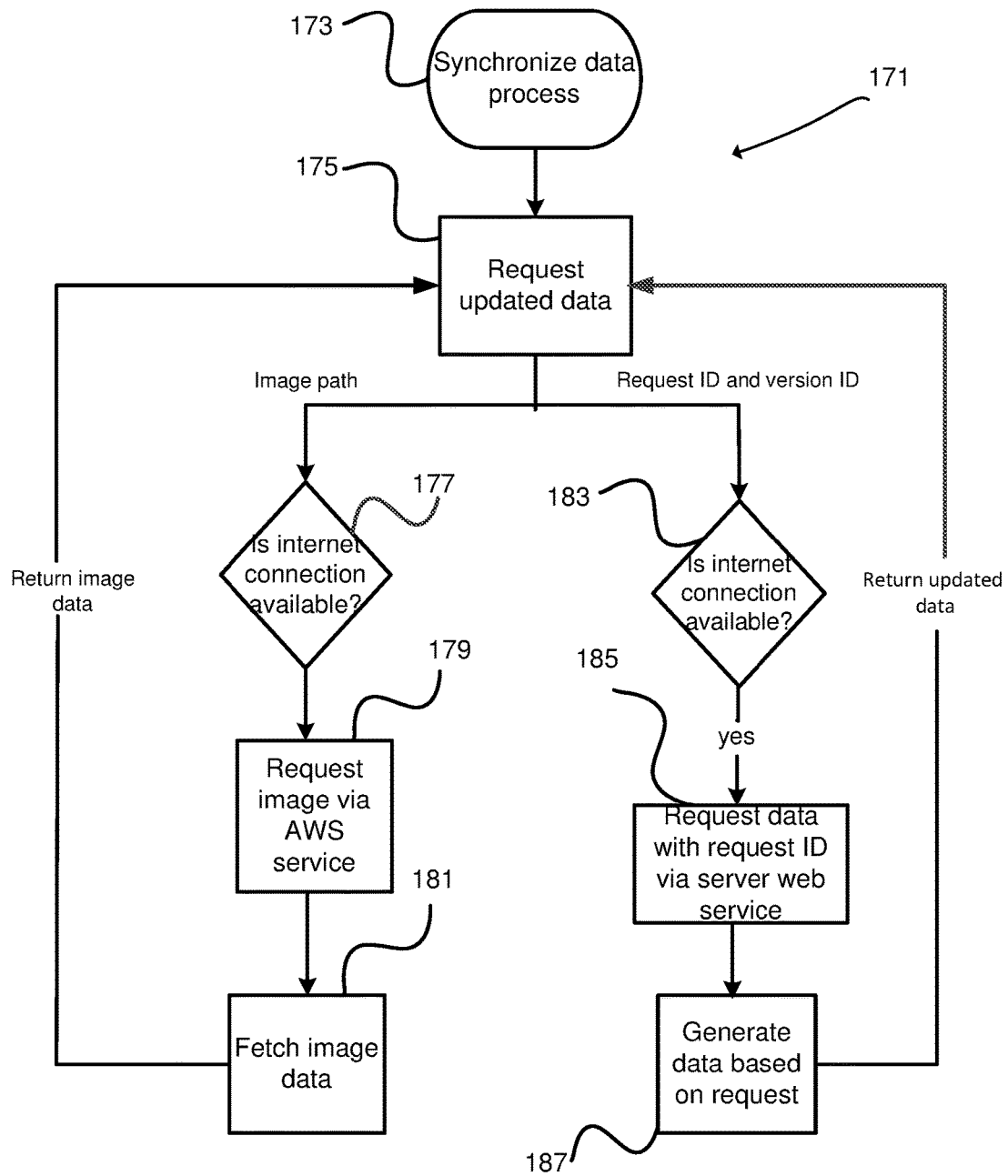
FIG. 14 is a flowchart showing the methodology of the Synchronize Hospital Data process of the builder application.

Selecting the Synchronize Hospital Data option 3.3 invokes a Synchronize Hospital Data process 171 of the builder application as shown in FIG. 14. The Synchronize Hospital Data process 171 is used for the App to synchronize local data to the system 11 via the server 14 when an action is performed on the tablet device 29'. Conversely, when the system data changes, each tablet device 29' will synchronize with the system 11 to update its local data to be consistent with the system data.

The Synchronize Hospital Data process 171 commences at step 173 and requests updated data at step 175 separately in the form of image data and hospital data associated with the particular Request ID as derived from the previous Initialize Hospital Data process 149. In the case of image data, the process follows an image path and checks whether an Internet connection is available at step 177. If so, then new image data is requested at step 179 via a cloud computing service such as AWS™ and the image data is fetched from its source in the cloud 13 at step 181. The new image data is then returned to the tablet device 29' for storage locally in the DBMS 53' and the process returns to the original request step 175 for exiting.

In the case of hospital data the process at step 175 obtains the Request ID and the version ID of the locally stored data and checks whether an Internet connection is available at step 183. If so, then the process requests new hospital data with the Request ID as appropriate from the system 11 via the server web service at step 185. The new hospital data is generated for download based on the request at step 187 and the hospital data is then returned to the tablet device 29' for updating locally in the DBMS 53'. The process returns to the original request step 175 for exiting.

Figure 15:
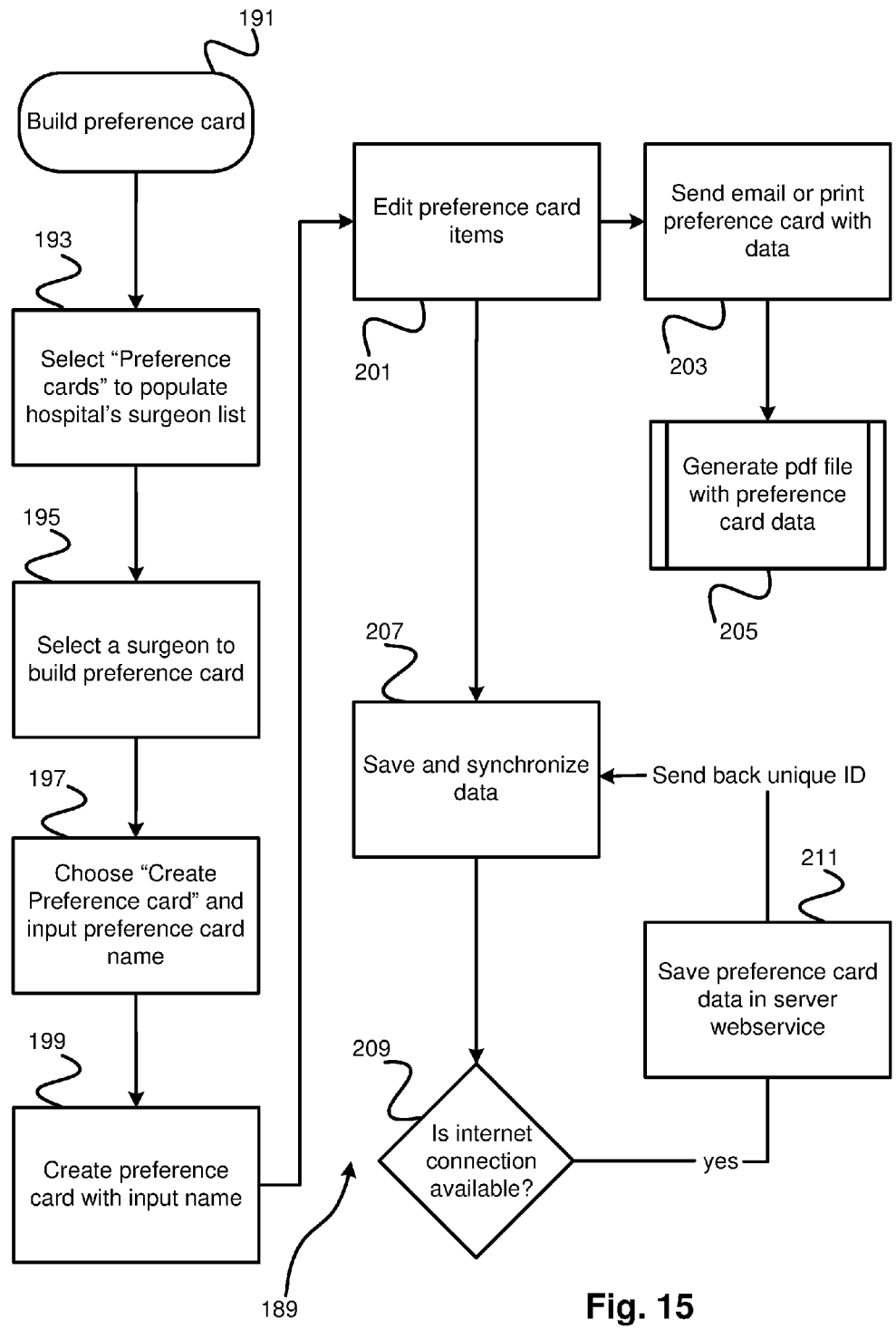
FIG. 15 is a flowchart showing the methodology of the Build Preference Card process of the builder application.

Selecting the Build Preference Card option 3.4 invokes a Build Preference Card process 189 of the builder application as shown in FIG. 15, where a preference card can be created, deleted, updated and searched using this option. The Build Preference Card process 189 commences at step 191 and allows a hospital manager 31 to select surgeons' preference cards to populate a hospital's surgeon list at step 193. From this list, the hospital manager 31 can select a surgeon to build a preference card for them at step 195. Once selected, the hospital manager can choose to create the preference and input the name of the preference card at step 197. When input, the preference card is created at step 199 and the process proceeds to allow editing of items for inclusion on the preference card at step 201. At this point, the Print and Email Preference Card option 3.5 can be invoked to send an email attaching the preference card to relevant staff or print it with the input data at step 203. Once step 203 is selected, a pdf file is generated with the preference card data displayed at step 205.

Following editing of the preference card at step 201, the process proceeds to allow saving and synchronizing of the preference card data with the system 11 at step 207. In order to achieve this, the process proceeds to check whether an Internet connection is available at step 209 and if so, saves the preference card data in the server web service at step 211, sending back the unique Request ID. The process then returns to the save and synchronize step 207 to exit.

As with the window application A, the builder application B also allows the hospital manager 31 to edit products using the Edit Products option 3.6 and edit the user profile using the Edit Profile option 3.7. These options adopt processes substantially analogous to the Manage Products option 2.5 and Manage Profile option 2.2 and will not be described further.

In describing the setup application C for use by a hospital nurse 33, the processes invoked by selecting Register Hospital App option 4.1, the Initialize Hospital Data option 4.2 and the Synchronize Hospital Data option 4.3 are substantially analogous to the corresponding options 3.1, 3.2 and 3.3 of the builder application B and will not be described further.

Figure 16:
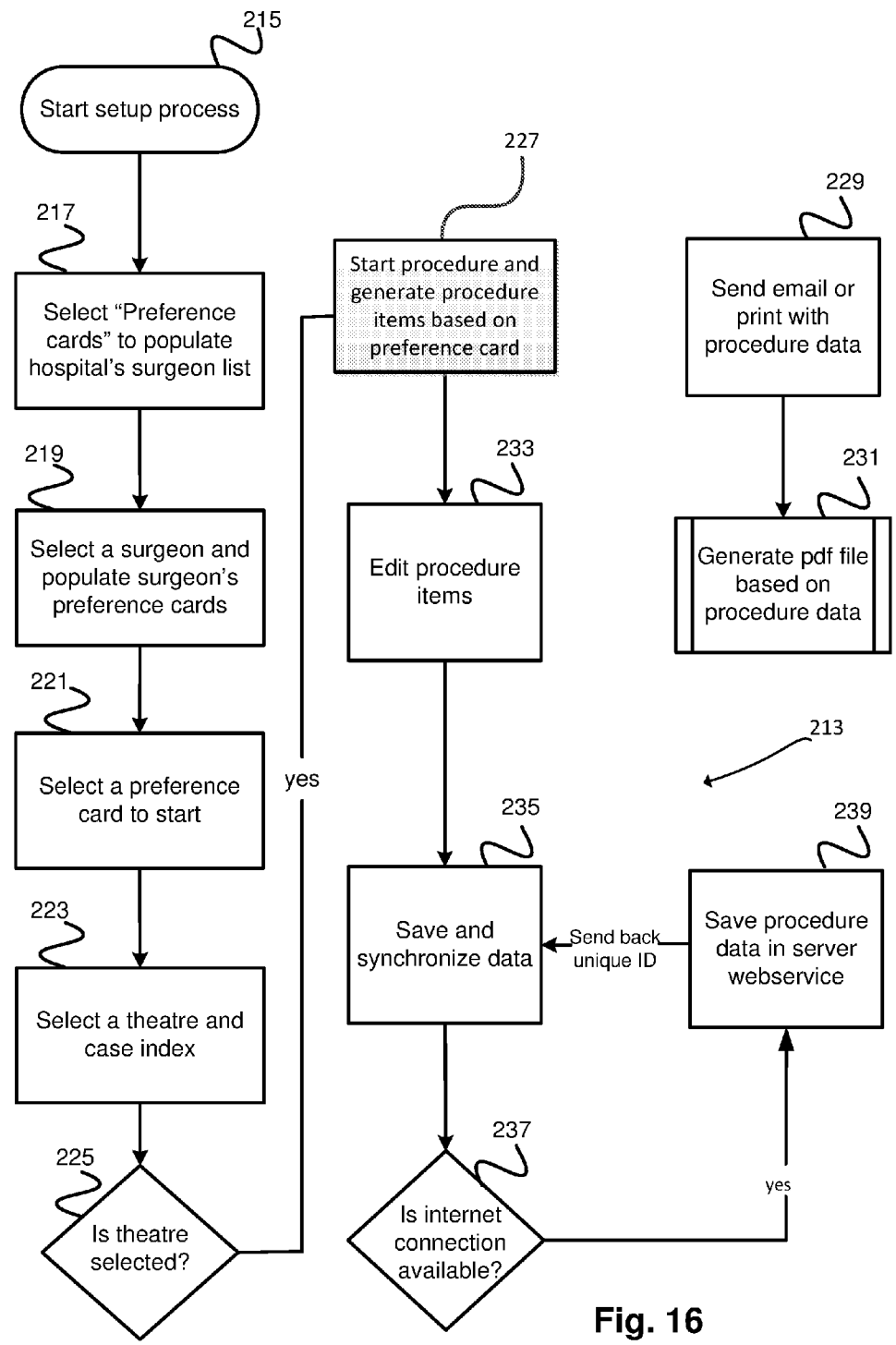
FIG. 16 is a flowchart showing the methodology of the Setup Procedure process of the setup application.

Selecting the Setup Procedure option 4.4 invokes a Setup Procedure process 213 of the setup application C as shown in FIG. 16, which is similar to the Build Preference Card process 189 of the builder application, but also different in important respects. The Setup Procedure process 213 allows a hospital nurse 33 to use preference cards which have been created and are pending population with object items, or which have completed population with object items. In order to create a surgical procedure record, a booking of a patient is required and interaction with the inventory system that stocks object items listed in the preference card is also required. Processes for these requirements will be subsequently described in detail.

The Setup Procedure process 213 commences at step 215 and allows the hospital nurse 33 to select surgeons' preference cards to populate a hospital's surgeon list at step 217. From this list, the hospital nurse 33 can select a surgeon to populate a particular surgeon's preference card with objects at step 219. It should be noted that in contrast to the hospital manager 31, the hospital nurse 33 is not able to build a surgeon's preference card for them.

Once selected, the hospital nurse 33 can select a preference card of that surgeon to start populating that card at step 221 with objects or items as required for a particular surgical procedure to be undertaken. Once the preference card has been populated, the process advances to allow the hospital nurse to select a theatre where the surgical procedure is to be performed and a case index is generated for the entry at step 223. The process checks for the theatre details to be entered at step 225 and once a theatre is selected the process advances to starting a surgical procedure record and generating object items for that procedure based on the selected and populated preference card at step 227. At this point, the Print and Email Preference Card option 4.5 can be invoked at step 229 to send an email attaching the procedure record or print it with the input data. Once step 229 is selected, a pdf file is generated with the procedure data displayed at step 231.

Following the procedure record starting step 227, the process proceeds to allow editing of procedure object items at step 233, which can then be saved and synchronized with the system 11 at step 235. In order to achieve this, the process proceeds to check whether an Internet connection is available at step 237 and if so, saves the procedure record data in the server web service at step 239, sending back the unique Request ID created for the Setup Procedure process instance. The process then returns to the save and synchronize data step 235 to exit.

Figure 17:
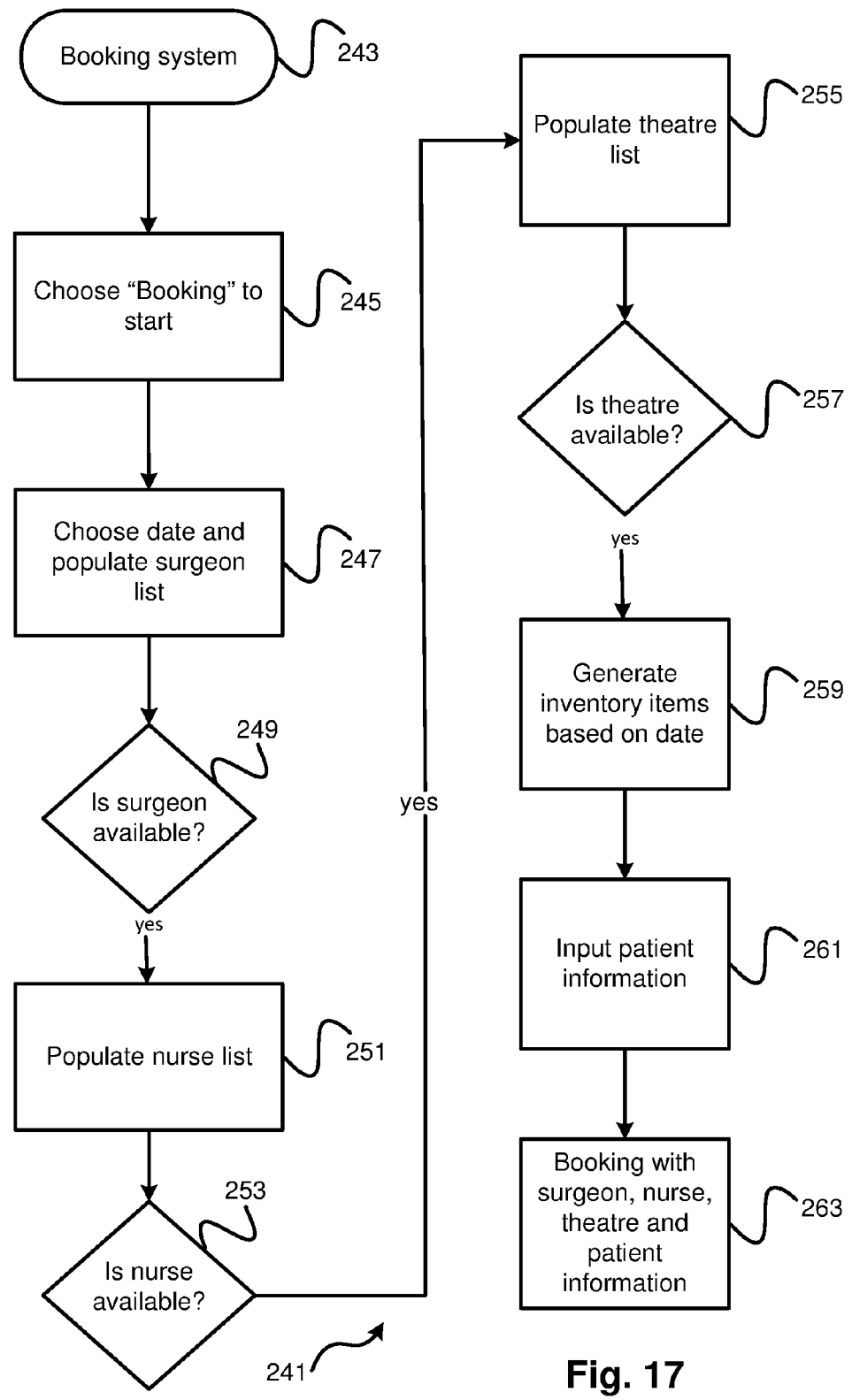
FIG. 17 is a flowchart showing the methodology of the Booking System process of the setup application.

After selecting the Setup Procedure option 4.4, the Booking System option 4.4.1 is selected, which invokes a Booking System process 241 as shown at FIG. 17. The Booking System process 241 is invoked after the Setup Procedure option 4.1 is completed and is performed with minimal interaction with the hospital nurse as a result of electronic data integration of booking system data with the hospital data stored on the data server 51.

The Booking System process 241 commences at step 243 and prompts the hospital nurse 33 to start the booking process at step 245. The process then either directs the hospital nurse to choose the date of the surgical procedure for which the preference card is applicable or retrieve this information from the booking system data integrated with the hospital data stored on the data server 51 and populate the surgeon list at step 247. The process then determines from accessing downloaded hospital data on the tablet device 29", whether the surgeon is available at step 249. If so, the process advances to either allow the hospital nurse 33 to populate a nurse list at step 251 with scrub nurses who would be appropriate to assist with the surgical procedure or automatically retrieve this information from the booking system data integrated with the hospital data stored on the data server. The process then determines whether the scrub nurse or nurses are available by accessing the hospital data of the tablet device 29" at step 253 and if so, advances to either prompting the nurse to populate a theatre list or retrieve this information automatically from the booking system data integrated with the hospital data stored on the data server at step 255. The process then determines whether a selected theatre is available at step 257 by accessing the hospital data on the tablet device 29". If so, the process advances to generating an inventory of object items required for the surgical procedure to be performed based on the chosen date of the procedure and the relevant preference card at step 259. Finally, the patient information is input at step 261 either manually by the nurse 33 or retrieved automatically from the booking system data integrated with the hospital data stored in the data server, and a booking record is made at step 263 with the surgeon, scrub nurse(s), theatre and patient information that has been selected.

The Inventory Management option 4.4.2 is also selected after completion of the Setup Procedure process 241, again with little or no interaction with the hospital nurse as a consequence of electronic data integration of inventory data with the hospital data stored on the data server 51.

Figure 18:
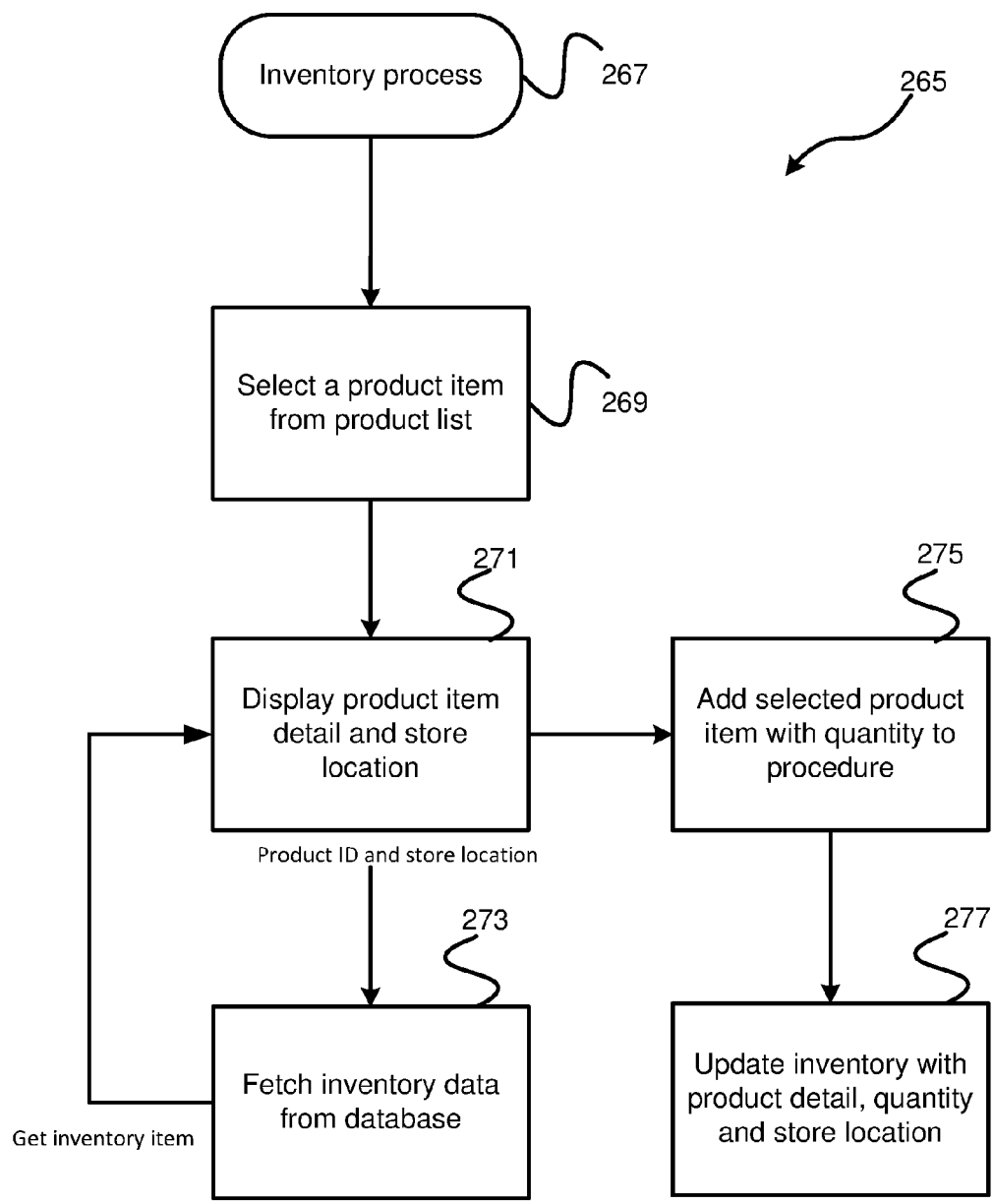
FIG. 18 is a flowchart showing the methodology of the Inventory Management process of the setup application.

Selecting the Inventory Management option 4.4.2 invokes an Inventory Management process 265 as shown in FIG. 18, which commences at step 267. The process proceeds to select a product (object) item from the product list at step 269 that has been recorded for the surgical procedure as a result of completion of the Setup Procedure process 241 and displays details at step 271 of the product item and the particular store location where the item is stored, normally either being in the surgical theatre storeroom or offsite at the hospital warehouse.

The Product ID and store location data is then used to fetch inventory data from the data server 51 at step 273 and a message sent to retrieve the inventory item for the recorded procedure. This is done invisibly and seamlessly from the perspective of the hospital nurse by electronic data integration and document/message exchange with a logistical support provider to the hospital. As shown in the drawing, steps 271 and 273 are performed iteratively for each product item listed in the procedure record until the list is exhausted.

Each selected product item, together with the quantity involved, is added to a final inventory record for the procedure at step 275 and the procedure record updated with information concerning the inventory status including the product detail, quantity and store location at step 277.

As with the builder application B, the setup application C also allows the hospital nurse 33 to edit the user profile using the Edit Profile option 4.6. This option adopts a process substantially analogous to the Edit Profile option 3.7 and will not be described further.

In describing the surgery application D for use by a scrub nurse 35, the processes invoked by selecting the Register Hospital App option 5.1, the Initialize Hospital Data option 5.2, the Synchronize Hospital Data option 5.3, the Booking System option 5.4.1, the Inventory Management option 5.4.2, the Print and Email Surgery Record 5.5 and Edit Profile 5.6 are substantially analogous to the corresponding options 4.1, 4.2, 4.3, 4.4.1, 4.4.2, 4.5 and 4.6 of the setup application C and will not be described further.

Figure 19:
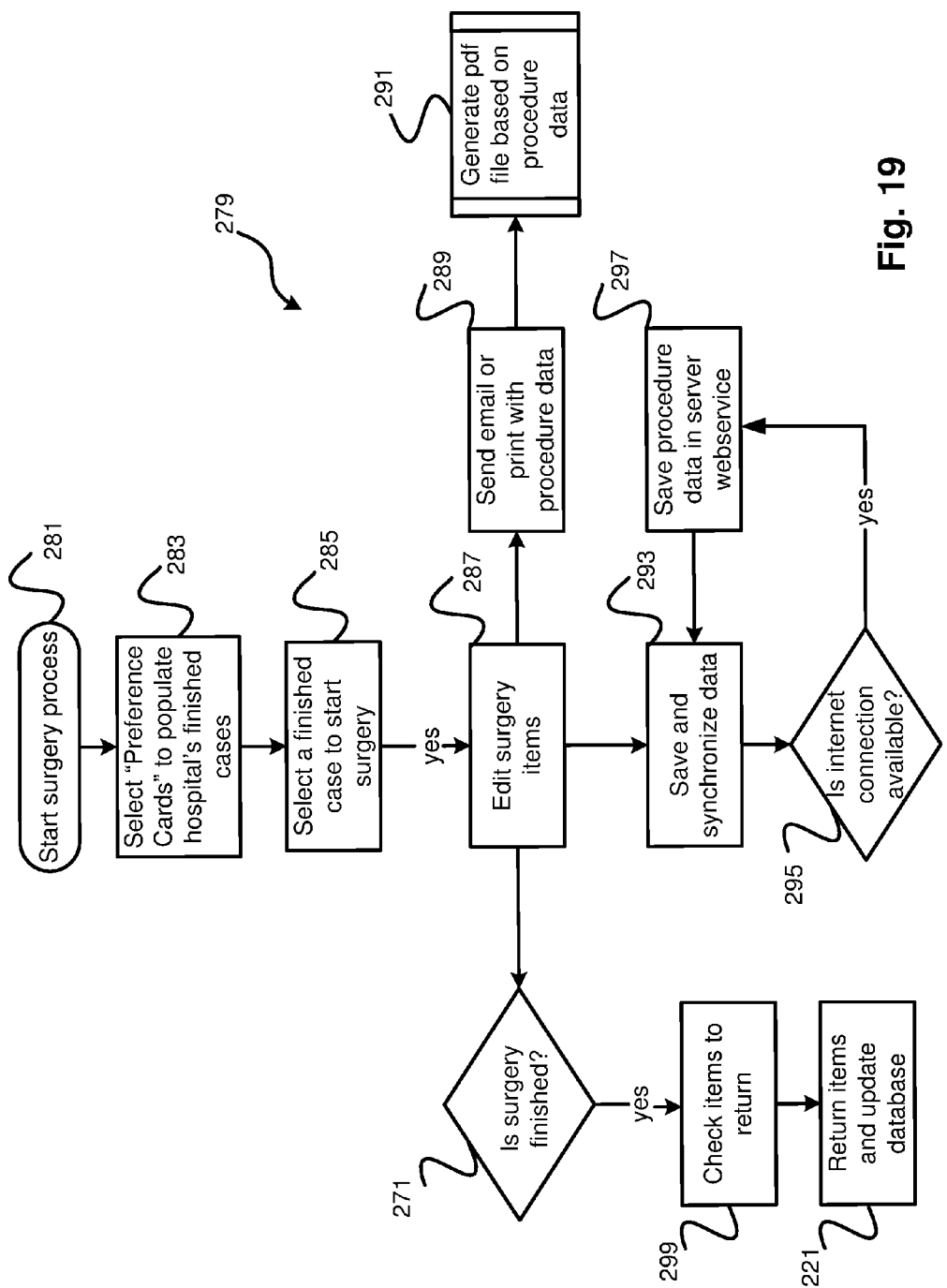
FIG. 19 is a flowchart showing the methodology of the Surgery Management process of the surgery application.
Figure 20:
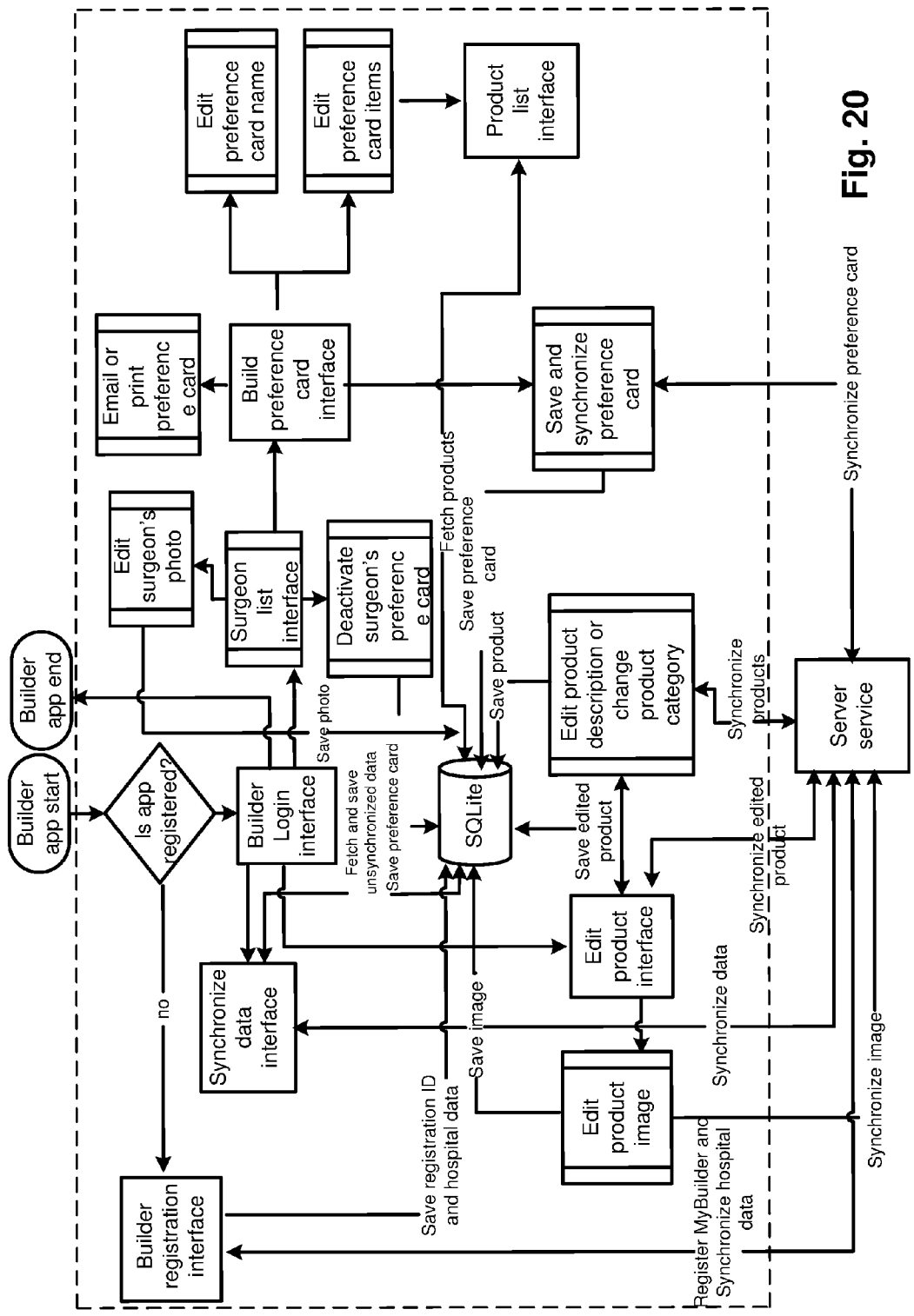
FIG. 20 is a flow diagram of the building application.
Figure 21:
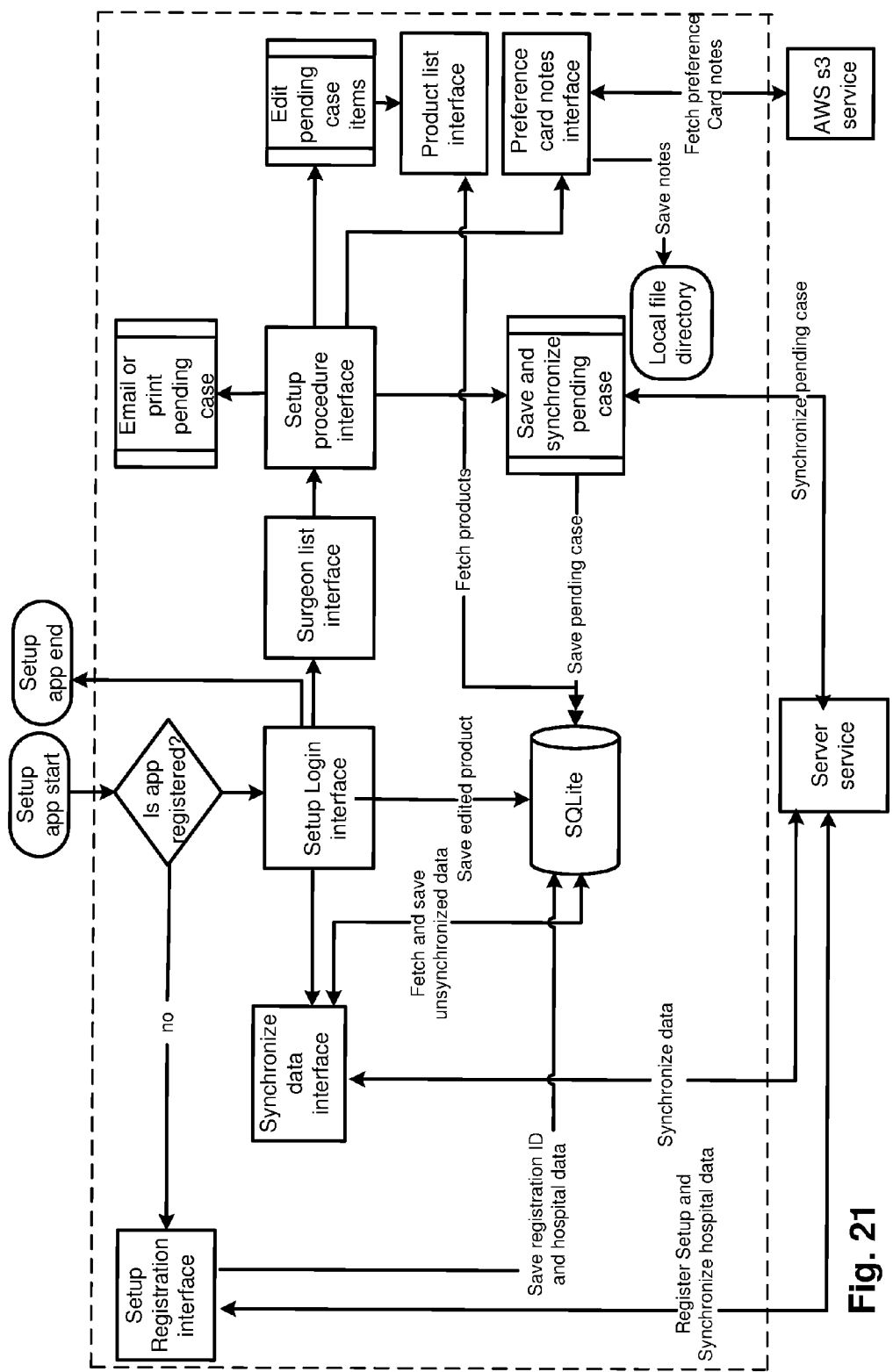
FIG. 21 is a flow diagram of the setup application.
Figure 22:
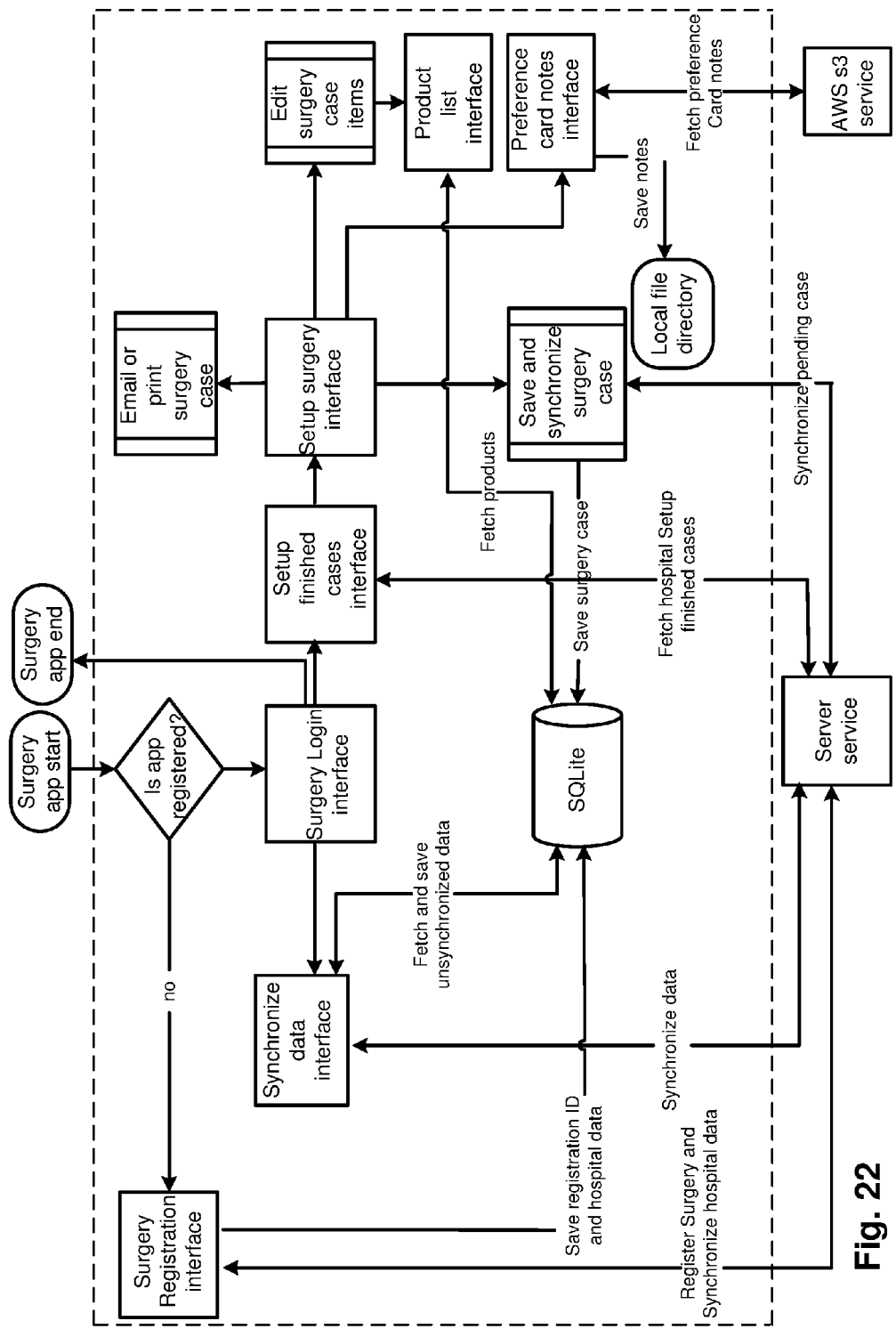
FIG. 22 is a flow diagram of the surgery application.
Figure 23:
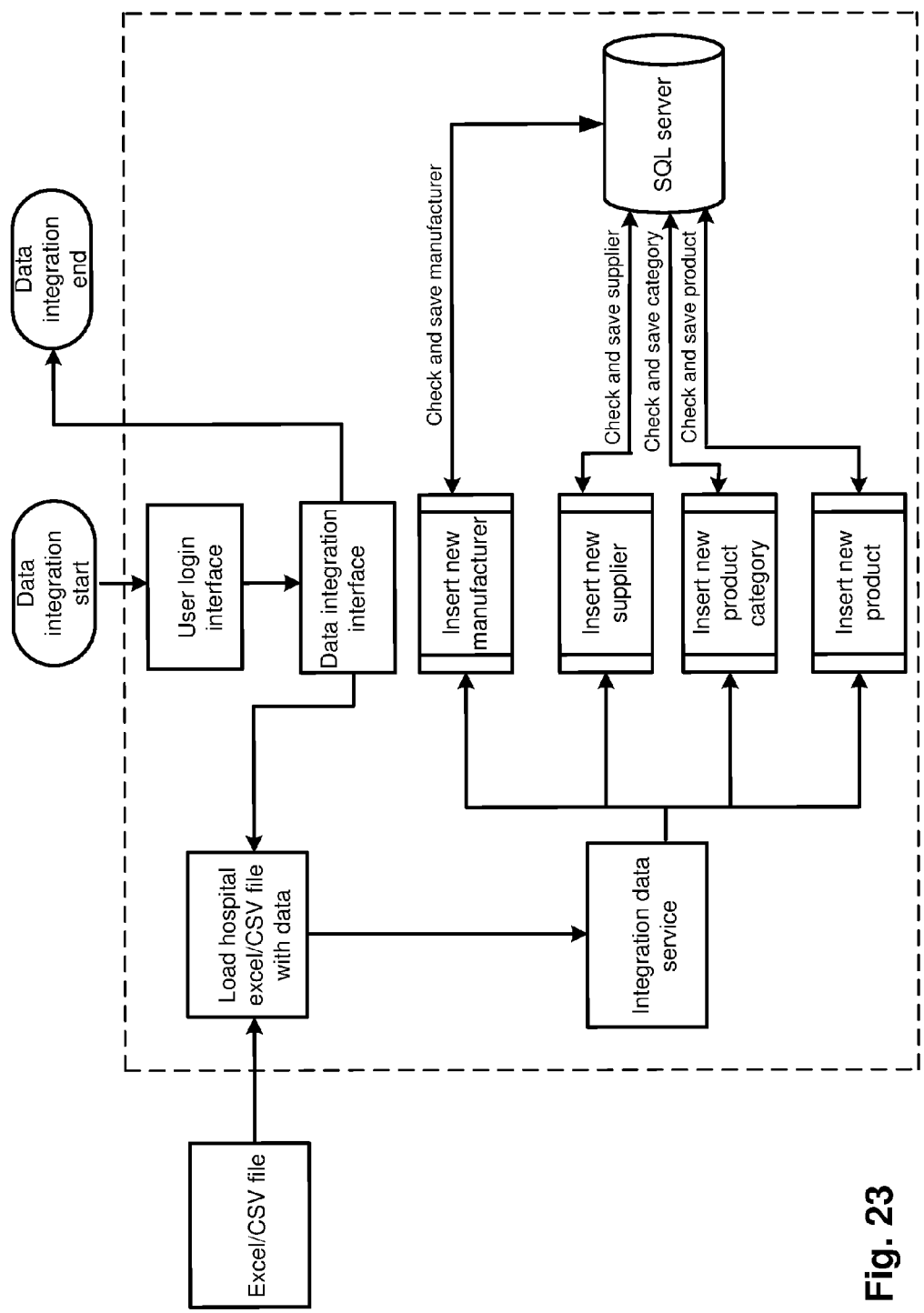
FIG. 23 is a flow diagram of the data integration workflow.
Figure 24:
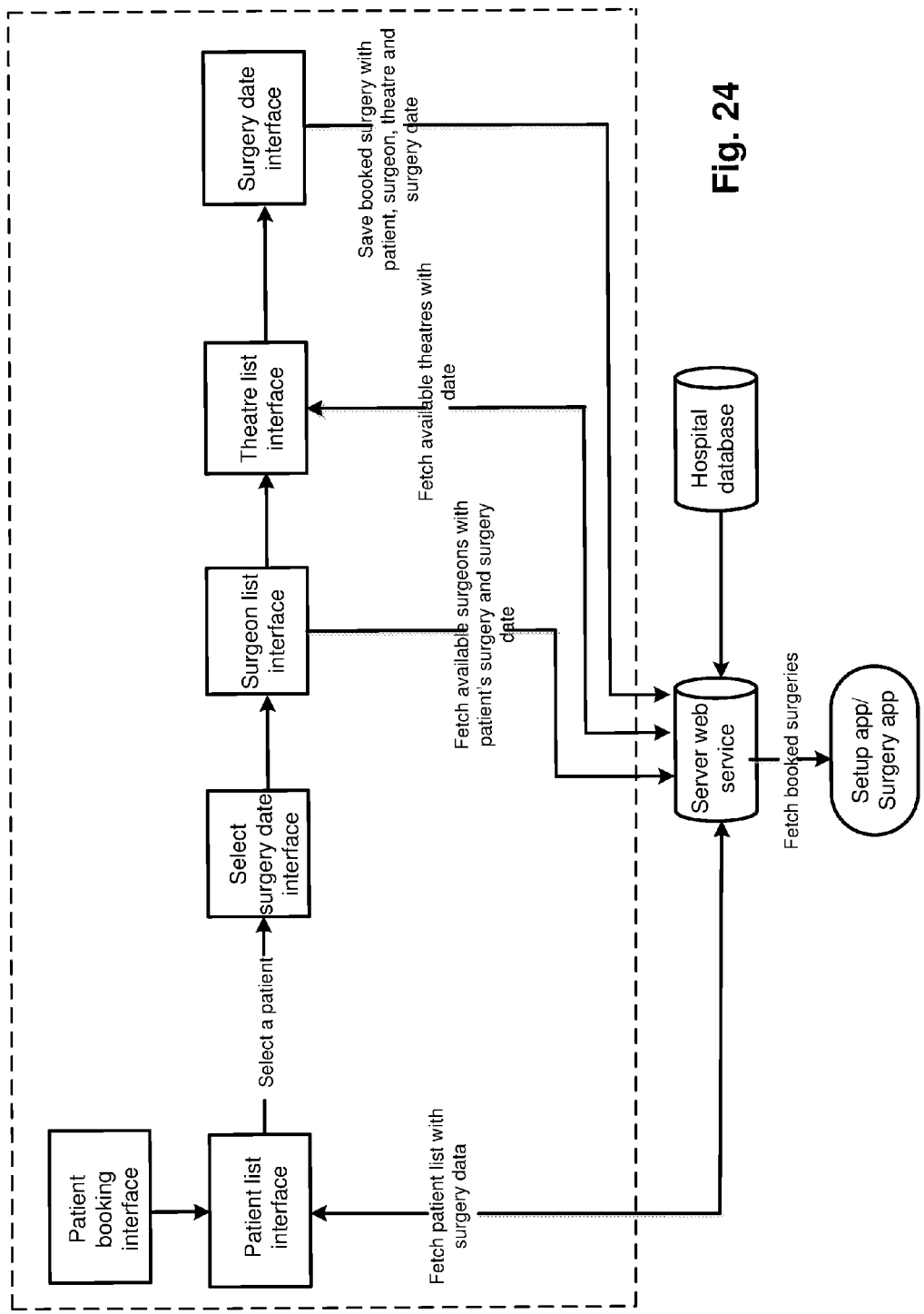
FIG. 24 is a flow diagram of the booking system workflow.
Figure 25:
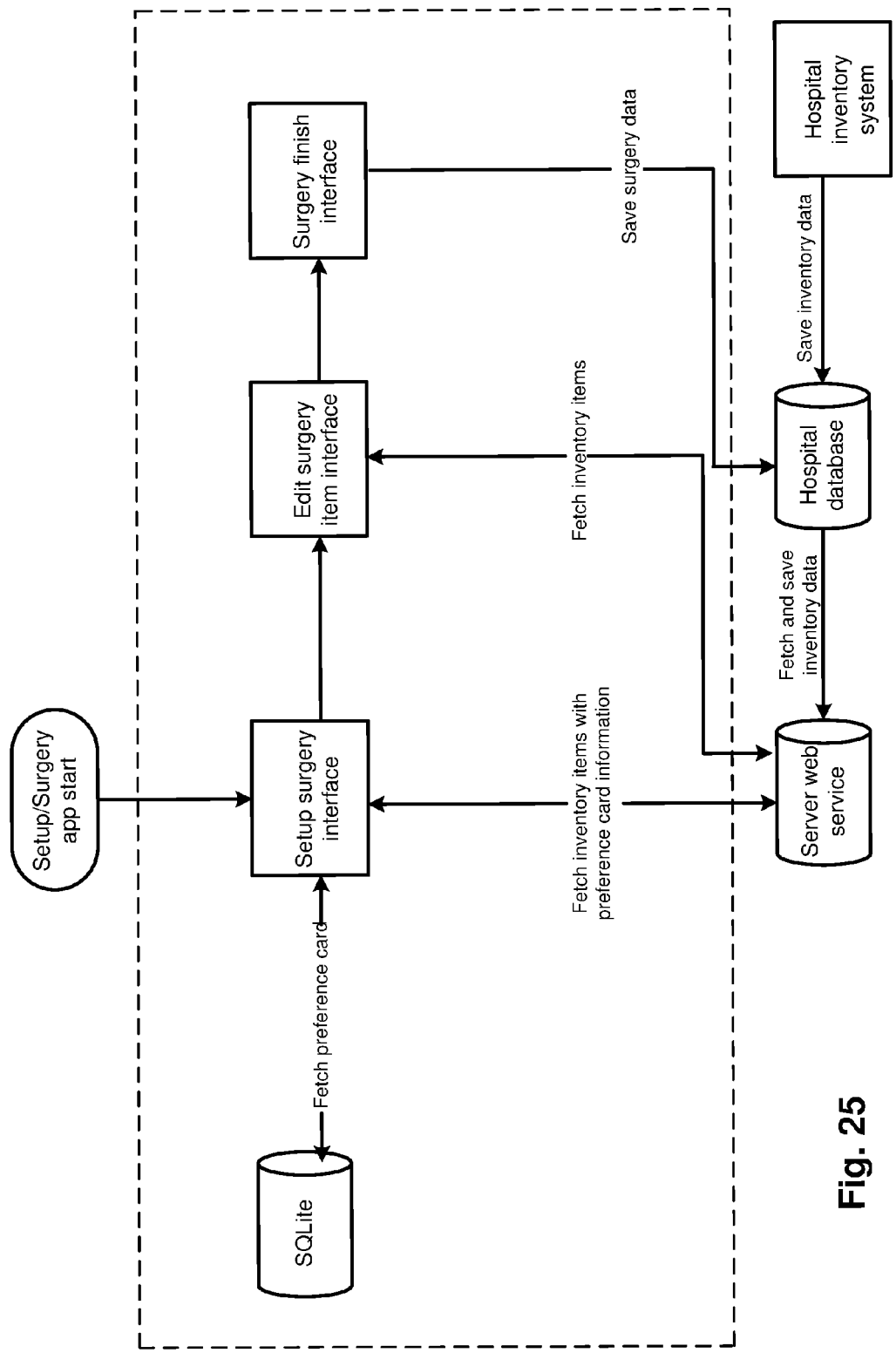
FIG. 25 is a flow diagram of the inventory management workflow.

Selecting the Setup Surgery option 5.4 invokes a Surgery Management process 279 of the surgery application D as shown in FIG. 19, which is similar to the Setup Procedure process 213 of the setup application, but also different in important respects. The Surgery Management process 279 allows a scrub nurse 35 to setup a surgical procedure using preference cards which have been created and are pending population with object items, or which have completed population with object items. As in the case of the setup application C, in order to create a surgical procedure record, a booking of a patient is required and interaction with the inventory system that stocks object items listed in the preference card is also required. Processes for these requirements are substantially the same as described with reference to the setup application, and as indicated previously, will not be further described.

The Surgery Management process 279 commences at step 281 and allows the scrub nurse 35 to select preference cards of a surgeon booked for surgery to populate the hospital's completed preference card case list at step 283. From this list, the scrub nurse 35 can select a finished preference card case to commence surgical procedure preparation and performance at step 285. The scrub nurse 35 can edit listed surgery items (objects) at step 287 as used during the surgery.

From this point, the scrub nurse 35 is presented with various options to complete the process. The scrub nurse can select the Print and Email Preference Card option 5.5 at step 289 and send an email attaching the procedure data to a relevant staff member or print same. Once step 289 is selected, a pdf file is generated with the procedure data displayed at step 291.

Alternatively, or additionally, the scrub nurse 35 can save and synchronize data during or at the completion of the surgical procedure at step 293. As previously described, the process then checks whether an Internet connection is available at step 295 and if so, saves the current procedure data at step 297 using the server web service and returns to the save and synchronize step 293 for exiting or further action.

The process to terminate prompts to see if the surgical procedure is finished at step 271, and if so checks the listed unused items that need to be returned to the storeroom at step 299. The process then prompts the scrub nurse at step 301 to return the unused items and updates the data server with the latest status concerning the unused items.

As implementation of the system 11 is reasonably complex from a software perspective, data flow diagrams are included at FIGS. 20 to 25 to show the data flow of the system as it applies for working with the builder application B, the setup application C the surgery application D, data integration involving external devices or systems, the booking system process and the inventory management system.

The diagrams are relatively self-explanatory and will not be described further.

User Interface Snapshots

FIGS. 26 to 29 depict snapshots of a user interface of the setup and surgery Apps on various interfaces.

Figure 26:

FIG. 26 depicts the Preference Card Setup Interface, and in particular the instance of the Pending cases. Pending hospital cases are requested from the App repository and uploaded to the interface.

Figure 27:
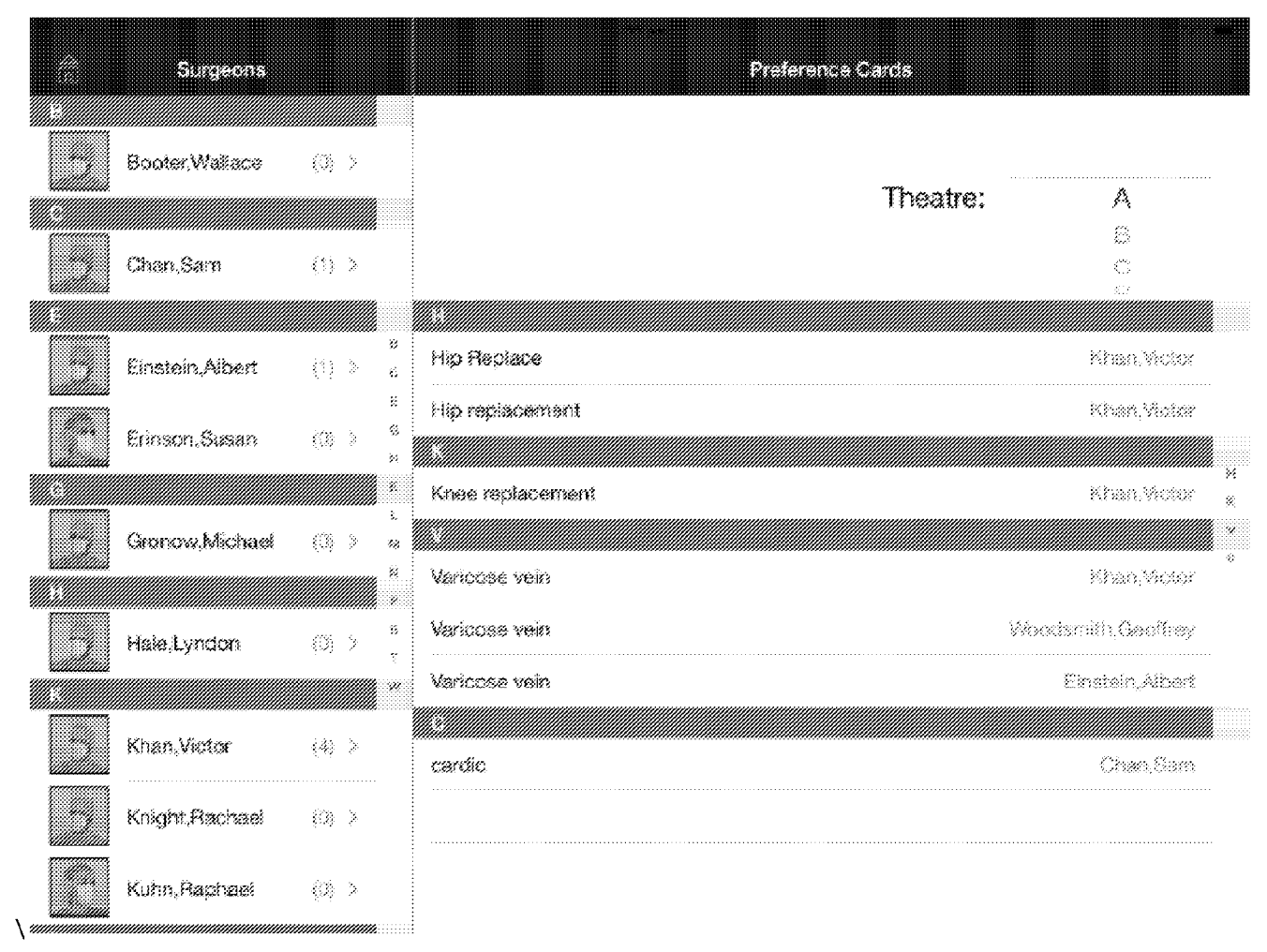

FIG. 27 depicts a user interface indicating preference cards for pending cases scheduled for Theatre A.

Figure 28:
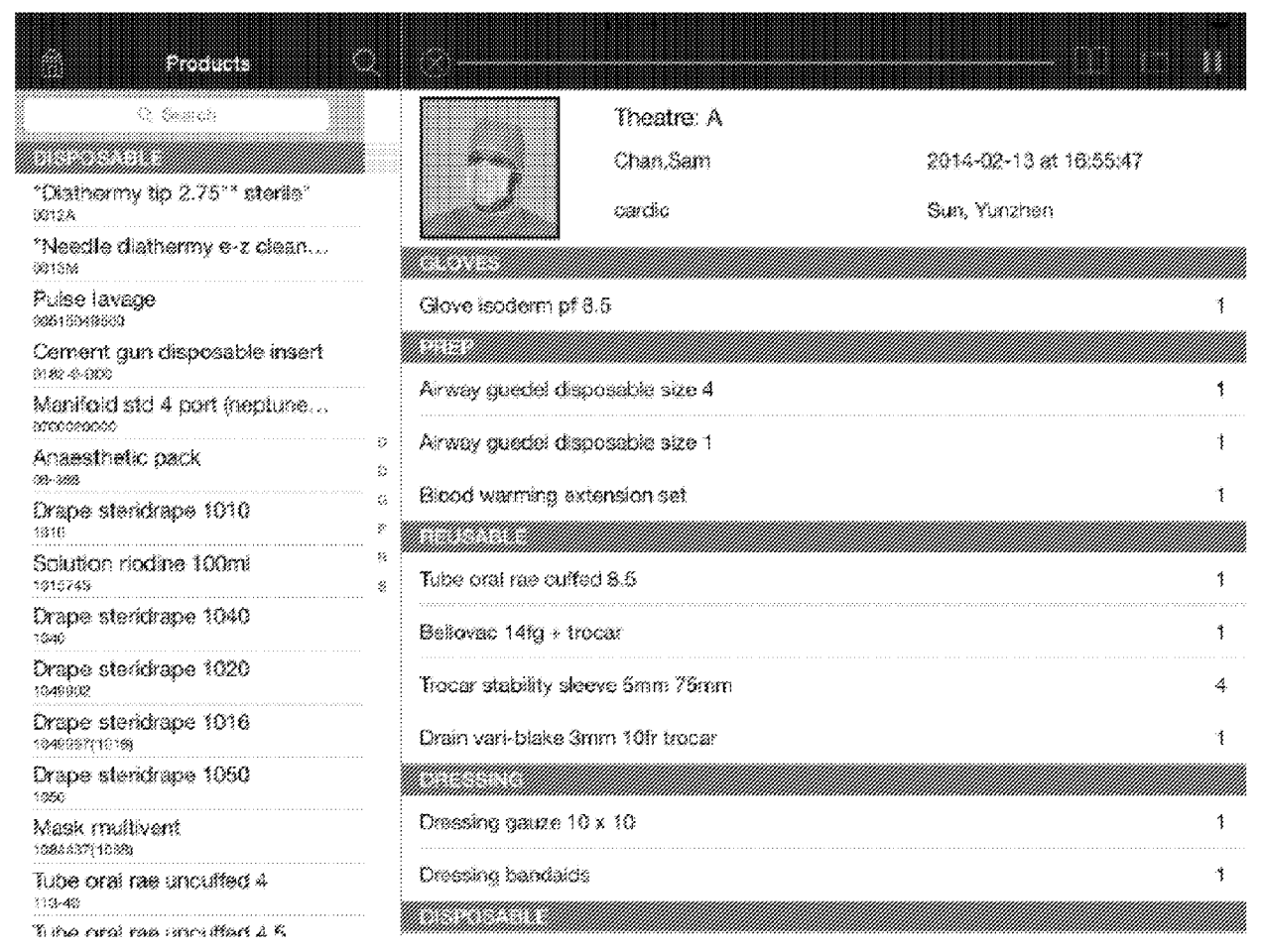

FIG. 28 depicts a user interface when the cardiac surgery is depicted in the user interface of FIG. 27. The user interface depicts product items (and quantities) stipulated by surgeon Dr Sam Chan's preference card for the cardiac surgery.

Figure 29:
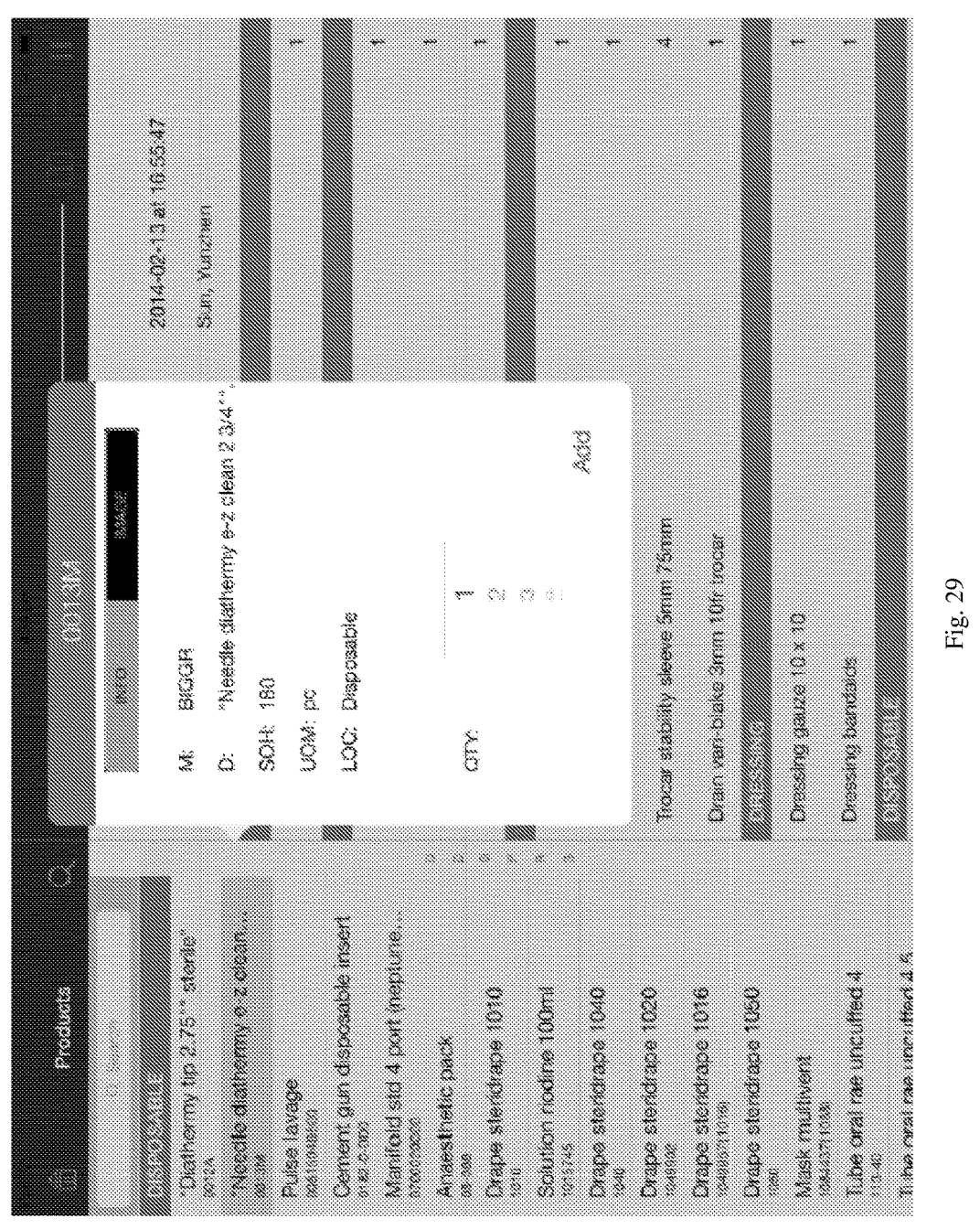

FIG. 29 depicts a user interface when the disposable product 'Needle diathermy e-z clean 2¾"' is selected from the listed disposable products in the user interface depicted in FIG. 28.

Various additions, modifications and substitutions regarding design and construction can be made without departing from the spirit and scope of the invention. In particular, other App modules are able to be integrated into the system and designed to provide a complete system and method for logistical management, support and supply of objects that can be enterprise wide, without the complexity and expense of current enterprise wide systems.

In particular the invention is not limited to application with hospitals, surgeon's or anaesthetist's preference cards and medical supplies, but can have equal application with objects of other types such as food, hardware, building materials, packaging, parcel delivery or the like where logistical considerations may apply.

The invention claimed is:

1. A system for providing logistical management, support and supply of medical supplies for consumption or use on a dynamic basis at one or more localities within a precinct or facility associated with the healthcare industry, wherein the precinct or facility sources the medical supplies from a store, the system comprising:
- (a) an external processing system defining an environment that is operable to allow access by a plurality of subscribers to relevant parts of a data store providing master data on medical supplies stored in the store;
- (b) a plurality of mobile devices for use by a plurality of types of the plurality of subscribers to setup templates defining the prescribed use of the medical supplies in a variety of situations in a dynamically scheduled manner;
- (c) a plurality of applications for operating on the plurality of mobile devices, each application being designed for a particular type of subscriber performing a prescribed task associated with the use of medical supplies in accordance with different templates and to download relevant parts of the data store to store locally on the devices;
- (d) each application adapted to progress the subscriber through a range of functions prescribed for the subscriber, the range of functions involving receiving inputs for dynamically scheduling the creation or performance of a medical procedure or both the creation and performance of the medical procedure using some of the medical supplies in accordance with a particular template, wherein some or all of the medical supplies may be used or consumed in the medical procedure;
- (e) at least one of the applications adapted to (i) track the use or consumption of the medical supplies in the procedure in real time, the use or consumption determined based on inputs received by one or more of the mobile devices from the subscribers, and (ii) receive a priority level associated with a category of product for stock ordering purposes, the at least one application adapted to update the external processing system and data store with status information relating to the medical supplies based on the real-time tracked use or consumption;
- (f) the external processing system communicating with an inventory management system to supplement the master data with information concerning the availability and whereabouts of all medical supplies that may be specified in a template and tracked in the store;
- (g) the external processing system communicating with a dynamic scheduling system to determine when a procedure defined by a particular template will occur; and
- (h) the external processing system organising the fetching of medical supplies for delivery to the particular locality at a prescribed time for use or consuming in a scheduled medical procedure pursuant to communication with the dynamic scheduling system, the invoking of an application and inputs received by one or more of the mobile devices during progression of the subscribers through the specified range of functions therefor.

2. The system as claimed in claim 1, wherein one of the applications is a building application for one type of subscriber to create templates for use and populating by other subscribers.

3. The system as claimed in claim 2, wherein another of the applications is a setup application for another type of subscriber to select one or more templates associated with a group of templates related to a particular type of procedure or person, and populating the template with appropriate objects to be used in a procedure defined by the template.

4. The system as claimed in claim 3, wherein a further of the applications is procedural application associated with a group of templates defining a finished list of medical supplies for use or consumption in a procedure; and updating the status of the medical supplies in real time after they are used or consumed; and updating the data store in relation to such status.

5. The system as claimed in claim 1, wherein the system is for a hospital, where the procedures are surgical procedures, and the templates are surgeon's preference cards.

6. A method for providing logistical management, support and supply of medical supplies for consumption or use on a dynamic basis at one or more localities within a precinct or facility associated with the healthcare industry, wherein the precinct or facility sources the medical supplies from a store, the system comprising:
- (a) defining, by an external processing system, an environment that is operable to allow access by a plurality of subscribers to relevant parts of a data store providing master data on medical supplies stored in the store;
- (b) one or more types of the plurality of subscribers setting up templates using a facility system defining the prescribed use of the medical supplies in a variety of situations in a dynamically scheduled manner;
- (c) using, by the facility system, different templates to prescribe task associated with the use of medical supplies and downloading relevant parts of the data store to store locally on the devices;
- (d) progressing, by at least one application executing on one of a plurality of mobile devices, one of the subscribers through a range of functions prescribed for the subscriber, the functions involving the creation or performance of a medical procedure or both the creation and performance of the procedure, using some of the medical supplies in accordance with a particular template, wherein some or all of the medical supplies may be used or consumed in the procedure;
- (e) tracking, by the at least one application, the use or consumption of the medical supplies in the procedure in real time, the use or consumption determined based upon inputs received from the subscribers, the at least one application receiving a priority level associated with a category of product for stock ordering purposes, and updating the external processing system and data store with status information relating to use of consumption of the medical supplies;
- (f) communicating, by the external processing system, with an inventory management system to supplement the master data with information concerning the availability and whereabouts of all medical supplies that may be specified in a template and tracked in the store;
- (g) communicating, by the external processing system, with a dynamic scheduling system to determine when a procedure defined by a particular template will occur; and
- (h) fetching, by the external processing system, medical supplies for delivery to the particular locality at a prescribed time for use or consuming in a scheduled medical procedure pursuant to communication with the dynamic scheduling system, the invoking of an application and data received by the one or more mobile devices during progression of the subscribers through the specified range of functions therefor.

* * * * *